United States Patent [19]

Nicolaides et al.

[11] Patent Number: 4,596,819

[45] Date of Patent: Jun. 24, 1986

[54] MODIFIED TRIPEPTIDES

[75] Inventors: Ernest D. Nicolaides; Francis J. Tinney; James S. Kaltenbronn; Dana E. DeJohn; Elizabeth A. Lunney; W. Howard Roark; Joseph T. Repine, all of Ann Arbor, Mich.

[73] Assignee: Warner-Lambert Company, Morris Plains, N.J.

[21] Appl. No.: 573,233

[22] Filed: Jan. 23, 1984

[51] Int. Cl.$^4$ .................... A61K 31/34; C07D 207/09; C07D 207/12; C07D 207/48

[52] U.S. Cl. .................... 514/423; 530/331; 514/424; 514/428; 544/372; 544/384; 548/531; 548/536; 548/537; 548/542; 548/568; 548/572; 560/25; 560/29; 560/153; 560/159; 560/160; 560/169; 530/315

[58] Field of Search ............... 548/531, 542, 572, 568; 514/423, 424, 428

[56] References Cited

U.S. PATENT DOCUMENTS

| | | | |
|---|---|---|---|
| 3,682,965 | 8/1972 | Hickner et al. | 548/542 X |
| 4,217,130 | 8/1980 | Tsuruta et al. | 548/542 X |
| 4,242,256 | 12/1980 | Sharpe et al. | 548/568 X |
| 4,325,943 | 4/1982 | Natarajan et al. | 548/533 X |
| 4,371,699 | 2/1983 | Ohashi et al. | 548/533 X |
| 4,402,969 | 9/1983 | Greenlee et al. | 548/533 X |
| 4,425,333 | 1/1984 | Iwao et al. | 548/533 X |
| 4,431,645 | 2/1984 | Smith et al. | 548/533 X |

Primary Examiner—Joseph Paul Brust
Attorney, Agent, or Firm—Ronald A. Daignault

[57] ABSTRACT

Modified oxytocin-vasopressin di- or tri-peptides wherein an amide group is replaced by a group selected from

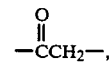

—CH$_2$NH—, —CH$_2$O—, —CH$_2$S—, —CH$_2$SO—, —CH$_2$SO$_2$—, —CH$_2$CH$_2$— and —CH=CH— are described as well as methods for their manufacture, pharmaceutical compositions and methods for treatment, especially of cognitive disorders, depression, morphine dependency and parkinsonism by adjunctive therapy.

7 Claims, No Drawings

MODIFIED TRIPEPTIDES

BACKGROUND OF THE INVENTION

Vasopressin, a neurohypophyseal nonapeptide which affects blood pressure and renal function, has been linked with areas in the brain implicated in cognitive function. Intranasal administration of vasopressin and a synthetic analog [1-desamino-8-D-arginine vasopressin (DDAVP)] has been reported to cause increases in learning and memory in young unimpaired human subjects when compared with placebo treatment. Three of four depressed patients demonstrated cognitive enhancement independent of changes in mood. Positive effects on recall of learned information have been reported in two patients given bilateral electroconvulsive shock therapy (ECT) while under the influence of desmopressin (DDAVP). Vasopressin and its analogs usually have been inactive by the oral route. The structures of arginine[8]-vasopressin (AVP), lysine[8]-vasopressin (LVP), oxytocin (OXY), and DDAVP are:

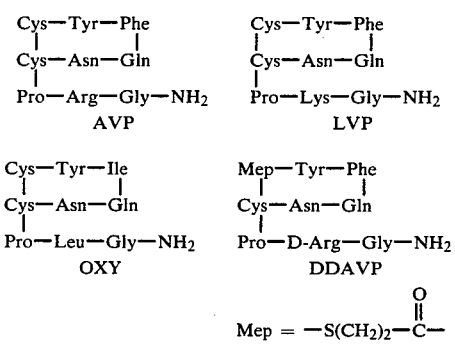

A series of vasopressin-oxytocin analogs were studied in two tests for effects on memory and/or learning. For the most part, active compounds were large peptides (8-12 amino acids). These studies also showed that various C-terminal di- and tripeptide fragments of vasopressin-oxytocin were effective in reversing puromycin-induced amnesia in mice. Pro-Arg-Gly-NH$_2$, the C-terminal fragment of AVP, has also been reported to be active in the rat pole-climbing avoidance test.

These studies indicate that the entire sequence of amino acids in vasopressin is not an essential requirement for memory and/or learning activity. Therefore, target memory and/or learning compounds could be modeled after the C-terminal tripeptides of vasopressin-oxytocin.

Peptides consist of chains formed by amino acids linked to each other by amide bonds.

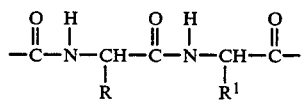

The amides, the side chains (R, R$^1$) and their stereochemical attachment control the overall conformation of the peptide that results in its biological activity.

Major disadvantages of peptides as drugs have been lack of oral activity and short duration of action.

The amide bonds are responsible for the primary metabolic instability of peptides. A few reports have appeared which describe the isosteric replacement of a single amide bond in a biologically important peptide. These isosteric analogs reportedly are more potent and possess greater metabolic stability than the parent peptide. However, the other amide bonds in the peptide are susceptible to enzymatic degradation. Analogs in which all of the amide bonds have been replaced by an isosteric group have not been reported to date. Such analogs should be resistant to proteolysis and possess greater oral activity. In addition, they also should have greater lipid solubility which would lead to higher concentrations in the central nervous system.

Prolyl-leucyl-glycine (PRO-LEU-GLY) analogs have been described at the Eighth American Peptide Symposium, May 22-27, 1983 in Tucson, Ariz. T. C. Case, et al., described PRO-D-LEU-GLY-NH$_2$ and PRO-D-LEU-GLY-NHEt as being potentially useful in treating neurological patients with movement disorders as an adjunctive drug associated with long-term administration of levodopa or other similar drugs used in treating parkinsonism.

D. Tourwe, et al., has disclosed, at the same symposium, Pro-Leu-Gly-NH$_2$ analogs in which the Leu-Gly peptide bond has been replaced by either CH$_2$NH, CH=CH or C≡C bonds. These compounds as MIF (melanocyte inhibitory factor) analogs are potential antidepressants.

SUMMARY OF THE INVENTION

The present invention relates to modified oxytocin-vasopressin di- or tri-peptides used for treating cognitive disorders, as antidepressants, in adjunct therapy for parkinsonism or in inhibiting morphine dependency and tolerance. The peptides are modified as isosteres in that one or more amide groups

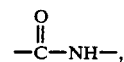

linking two amino acids in the peptide chain may be replaced by a group selected from

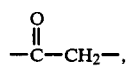

—CH$_2$—NH—, —CH$_2$—O—, —CH$_2$—S—, —CH$_2$SO—, —CH$_2$SO$_2$—, —CH$_2$CH$_2$—, and —CH=CH—.

Accordingly, the present invention is a modified peptide wherein (a) at least one amide bond in the peptide chain is replaced by a group selected from

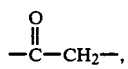

—CH$_2$—NH—, —CH$_2$—O—, —CH$_2$—S—, —CH$_2$SO—, —CH$_2$SO$_2$—, —CH$_2$CH$_2$— and —CH=CH—; (b) the chain contains two or three amino acids selected from the group consisting of proline, 4-hydroxyproline, 4-ketoproline, 5-ketoproline, glutamine, pyroglutamic acid, leucine, phenylalanine, lysine, glycine, arginine, and serine; (c) the chain may further contain a group selected from 2-nicotinoyl, 5-methyl-2-thiophenecarbonyl and

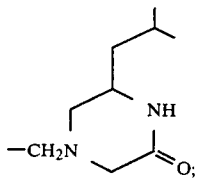

(d) a terminal amino group may be unsubstituted or substituted by a protecting group; (e) a terminal carboxyl group may be a free acid, a lower alkyl or benzyl ester, an amide, a lower alkyl, di-lower alkyl amide, or a lower alkylthioalkylene amide; or (f) a terminal group may be hydroxymethyl or aminomethyl, and a pharmaceutically acceptable acid addition or base salt thereof.

The present invention includes a pharmaceutical composition comprising an effective amount of the above modified peptide in admixture with a pharmaceutically acceptable carrier or excipient, and a method for treating cognitive disorders in patients suffering therefrom comprising administering to said patient the above pharmaceutical composition in unit dosage form.

The present invention also includes novel intermediates used to manufacture the novel tripeptides. Some of these dipeptides are included within the compounds of formula I.

DETAILED DESCRIPTION

Particular protecting groups contemplated for the terminal amino group on the above-defined modified peptide are carbobenzoxy (Z), t-butoxycarbonyl (t-BOC), tosyl or p-methoxybenzyloxycarbonyl.

The term "lower" alkyl is intended to mean a straight or branched hydrocarbon chain having from 1 to 4 carbon atoms, such as methyl, ethyl, n-propyl, i-propyl, butyl, sec-butyl, or t-butyl.

Alkylene is intended to mean a straight hydrocarbon chain of 2 to 4 carbon atoms and, particularly, ethylene.

Particular modified peptides of the present invention are those of the formula

Pro-[ ]-Leu-[ ]-Gly    I wherein at least one [ ] represents a replacement for an amide bond by a group selected from

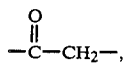

—CH$_2$—NH—, —CH$_2$—O—, —CH$_2$S—, —CH$_2$SO—, —CH$_2$SO$_2$—, —CH$_2$CH$_2$— and —CH=CH—, the other [ ] being —CO—NH—; the terminal amino group may be unsubstituted or substituted as defined above, and the terminal carboxyl group may be a free acid, ester or amide as defined above.

Another modified peptide of the present invention is a compound of the formula

Pro-[ ]-Lys-[ ]-Gly    II wherein at least one [ ] represents a replacement for an amide bond by a group as defined above, the other [ ] being —CONH—; the terminal amino group may be unsubstituted or substituted as defined above, and the terminal carboxyl group may be a free acid, ester or amide as defined above.

Specific embodiments of the present invention are the following:

[S-(R*,R*)]-phenylmethyl 2-[[[1-[[[2-(1,1-dimethylethoxy)-2-oxoethyl]thio]methyl]-3-methylbutyl]amino]carbonyl]-1-pyrrolidinecarboxylate;

[2S-(R*,R*)]-phenylmethyl 2-[[[1-[[(carboxymethyl)thio]methyl]-3-methylbutyl]amino]carbonyl]-1-pyrrolidinecarboxylate;

[S-(R*,R*)]-phenylmethyl 2-[[[1-[[(2-amino-2-oxoethyl)thio]methyl]-3-methylbutyl]amino]carbonyl]-1-pyrrolidinecarboxylate;

[S-(R*,R*)]-phenylmethyl 2-[[[1-[[[2-(1,1-dimethylethoxy)-2-oxoethyl]thio]methyl]-3-methylbutyl]amino]carbonyl]-4-oxo-1-pyrrolidinecarboxylate;

[S-(R*,R*)]-phenylmethyl 2-[[[1-[[(carboxymethyl)thio]methyl]-3-methylbutyl]amino]carbonyl]-4-oxo-1-pyrrolidinecarboxylate;

(S)-1,1-dimethylethyl[[4-methyl-2-[[(5-methyl-2-thienyl)carbonyl]amino]pentyl]thio]acetate;

(S)-[[4-methyl-2-[[(5-methyl-2-thienyl)carbonyl]amino]pentyl]thio]acetic acid;

[S-(R*,R*)]-phenylmethyl 5-oxo-2-[[[1-[[[2-(1,1-dimethylethoxy)-2-oxoethyl]thio]methyl]-3-methylbutyl]amino]carbonyl]-1-pyrrolidinecarboxylate;

[S-(R*,R*)]-1,1-dimethylethyl[[4-methyl-2-[[(5-oxo-2-pyrrolidinyl)carbonyl]amino]pentyl]thio]acetate;

[S-(R*,R*)]-phenylmethyl 5-oxo-2-[[[1-[[(carboxymethyl)thio]methyl]-3-methylbutyl]amino]carbonyl]-1-pyrrolidinecarboxylate;

(S)-1,1-dimethylethyl[[4-methyl-2-[(2-pyridinylcarbonyl)amino]pentyl]thio]acetate;

(S)-[[4-methyl-2-[(2-pyridinylcarbonyl)amino]pentyl]thio]acetic acid monohydrochloride;

[S-(R*,R*)]-phenylmethyl 2[[[1-[[[2-(1,1-dimethylethoxy)-2-oxoethyl]sulfonyl]methyl]-3-methylbutyl]amino]-carbonyl]-1-pyrrolidinecarboxylate.

[S-(R*,R*)]-2-[[[1-[[(carboxymethyl)sulfonyl]methyl]-3-methylbutyl]amino]carbonyl]-1-pyrrolidinecarboxylic acid;

[S-(R*,R*)]-1,1-dimethylethyl[[2-[[[1-(4-methoxybenzoyl)-2-pyrrolidinyl]carbonyl]amino]-4-methylpentyl]thio]acetate;

[S-(R*,R*)]-[[2-[[[1-(4-methoxybenzoyl)-2-pyrrolidinyl]carbonyl]amino]-4-methylpentyl]thio]acetic acid;

[S-(R*,R*)]-phenylmethyl 2-[[[1-[[(2-amino-2-oxoethyl)amino]-methyl]-3-methylbutyl]amino]carbonyl]-1-pyrrolidinecarboxylate, monohydrochloride;

[S-(R*,R*)]-N-[4-methyl-2-[[(5-oxo-2-pyrrolidinyl)carbonyl]amino]pentyl]glycine, monohydrochloride;

[S-(R*,R*)]-4-(2-amino-4-methylpentyl)-6-(2-methylpropyl)-2-piperazinone, dihydrochloride;

[2S-[2R*,4[R*(R*)]]]-phenylmethyl 2-[[[3-methyl-1-[[3-(2-methyl-propyl)-5-oxo-1-piperazinyl]methyl]butyl]amino]carbonyl]-1-pyrrolidinecarboxylate, monohydrochloride;

[2S-[2R*,4[R*(R*)]]]-N-(3-methyl-1-[[3-(2-methylpropyl)-5-oxo-1-piperazinyl]methyl]butyl]-5-oxo-2-pyrrolidinecarboxamide, monohydrochloride;

[S-(R*,R*)]-phenylmethyl 2-[[[1-[[2-(1,1-dimethylethoxy)-2-oxoethoxy]methyl]-3-methylbutyl]amino]-carbonyl]-1-pyrrolidinecarboxylate;

[S,-(R*,R*)]-phenylmethyl 2-[[[1-[(carboxy)methoxy]-3-methylbutyl]amino]carbonyl]-pyrrolidinecarboxylate;

(2S)-phenylmethyl 2-[[[1-[[2-(1,1-dimethylethoxy)-2-oxoethoxy]methyl]-2-phenylethyl]amino]carbonyl]-1-pyrrolidinecarboxylate;

(2S)-phenylmethyl 2-[[[1-[(carboxymethoxy)methyl]-2-phenylethyl]amino]carbonyl]-1-pyrrolidinecarboxylate;

(S)-phenylmethyl 2-[[1-[[[2-(1,1-dimethylethoxy)-2-oxoethyl]amino]carbonyl]-3-methylbutoxy]methyl]-1-pyrrolidinecarboxylate;

(S)-phenylmethyl 2-[[1-[[(carboxymethyl)amino]carbonyl]-3-methylbutoxy]methyl]-1-pyrrolidinecarboxylate;

(2S)-phenylmethyl 2-[[1-[[(2-ethoxy-2-oxoethyl)amino]carbonyl]-3-methylbutoxy]methyl]-1-pyrrolidinecarboxylate;

(2S)-phenylmethyl 2-[[1-[[(2-amino-2-oxoethyl)amino]carbonyl]-3-methylbutoxy]methyl]-1-pyrrolidinecarboxylate;

(2S)-phenylmethyl 2-[[1-[[(2-amino-2-oxoethyl)amino]carbonyl]-3-methylbutoxy]methyl]-1-pyrrolidinecarboxylate;

(S)-phenylmethyl 2-[[[(carboxymethyl)amino]carboxy]methoxy]methyl]-1-pyrrolidinecarboxylate;

N-[N-[[1-[(4-methylphenyl)sulfonyl]-2-pyrrolidinyl]methyl]-L-leucyl]glycine, hydrochloride;

(S)-1,1-dimethylethyl N-[N-[[1-[(4-methylphenyl)sulfonyl]-2-pyrrolidinyl]methyl]-L-leucyl]-glycinate;

(S)-$N^2$-[[1-[(4-methylphenyl)sulfonyl)-2-pyrrolidinyl]-methyl]-D-leucyl]-glycinamide;

[2S-[2R*-(2R*,4R*)]]-N-[4-methyl-2-[[[1-[(4-methylphenyl)sulfonyl]-2-pyrrolidinyl]methyl]amino]pentyl]glycine, dihydrochloride;

[S-(R*,R*)]-N-[4-methyl-2-[[[1-[(4-methylphenyl)sulfonyl]-2-pyrrolidinyl]carbonyl]amino]pentyl]glycine, monohydrochloride;

[S-(R*,R*)]-phenylmethyl 2-[[[1-[[(2-amino-2-oxoethyl)amino]carbonyl]-3-methylbutyl]amino]methyl]-1-pyrrolidinecarboxylate;

[S-(R*,R*)]-phenylmethyl 2-[[[1-[(1,1-dimethylethoxy)carbonyl]-3-methylbutyl]amino]methyl]-1-pyrrolidinecarboxylate;

[S-(R*,R*)]-phenylmethyl 2-[[(1-carboxy-3-methylbutyl)amino]methyl]-1-pyrrolidinecarboxylate, hydrochloride;

[S-(R*,R*)]-phenylmethyl 2[-[[[1-[(2-amino-2-oxoethyl)amino]carbonyl]-3-methylbutyl]amino]methyl]-1-pyrrolidinecarboxylate;

[S-(R*,R*)]-1-phenylmethyl 2-[[[1-[[(carboxymethyl)thio]methyl]-3-methylbutyl]amino]-methyl]-1-pyrrolidinecarboxylate;

[S-(R*,R*)]-1-phenylmethyl 2-[[[1-[[(2-amino-2-oxoethyl)thio]methyl]-3-methylbutyl]amino]methyl]-monohydrochloride, 1-pyrrolidinecarboxylate;

[S-(R*,R*)]-phenylmethyl 2-[[[1-(hydroxymethyl)-5-[[(phenyl-methoxy)carbonyl]-amino]pentyl]amino]-carbonyl]-1-pyrrolidinecarboxylate;

[S-(R*,R*)]-1,1-dimethylethyl 2-[[[1-[[(2-amino-2-oxoethyl)amino]carbonyl]-5-[[(phenylmethoxy)carbonyl]amino]pentyl]amino]methyl]1-pyrrolidinecarboxylate;

[S-(R*,R*)]-2-[[[1-[[(carboxymethyl)amino]methyl]-3-methylbutyl]amino]-methyl]-1-pyrrolidinecarboxylate, phenylmethyl ester, hydrochloride;

(S)-N-[$N^6$-[(phenylmethoxy)carbonyl]-$N^2$(2-pyrrolidinylmethyl)]-D-lysylglycinamide, trifluoroacetate;

(S)-phenylmethyl 2-[[[[[(ethoxycarbonyl)methyl]amino]carbonyl]methoxy]methyl]-1-pyrrolidinecarboxylate;

(S)-phenylmethyl 2-[[[[(2-amino-2-oxoethyl)amino]carbonyl]methoxy]methyl]-1-pyrrolidinecarboxylate;

(2S)-phenylmethyl 2[[[1-[(2-amino-2-oxoethoxy)methyl]-2-phenylethyl]amino]carbonyl]-1-pyrrolidinecarboxylate; and

[S-(R*,R*)]-phenylmethyl 2-[[[1-[(2-amino-2-oxoethoxy)methyl]-3-methylbutyl]amino]carbonyl]-1-pyrrolidinecarboxylate.

Because of the amphoteric nature of the compounds of the invention and the existence of either a free carboxylic acid group or a free amino group, the modified peptides of the invention are useful in a neutral form, i.e., amphoteric or zwitterionic where both a base and an acid group are present, a free acid form or a free base form or in the form of pharmaceutically acceptable salts thereof, both acid addition or base.

Appropriate pharmaceutically acceptable salts within the scope of the invention are those derived from mineral acids such as hydrochloric acid and sulfuric acid, and organic acids such as ethanesulfonic acid, benzenesulfonic acid, p-toluenesulfonic acid, and the like, giving the hydrochloride, sulfate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

Appropriate pharmaceutically acceptable base salts are those derived from inorganic bases, metal cations, and organic bases, such as amines. Metallic salts contemplated are, for example, sodium, potassium, magnesium, calcium, aluminium, zinc, iron, and the like. Organic bases contemplated are positively charged ammonium ion and analogous ions of the formula:

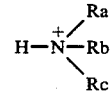

wherein Ra, Rb, and Rc, independently may be alkyl of from one to six carbon atoms, cycloalkyl of from about three to six carbon atoms, aryl, aralkyl of from about seven to about ten carbon atoms, hydroxyalkyl of from two to four carbon atoms, or monoarylhydroxyalkyl of from about 8 to about 15 carbon atoms. Further, when taken together with the nitrogen atom to which they are attached, any two of Ra, Rb, and Rc may form part of a 5-membered or 6-membered nitrogen heterocyclic aromatic or nonaromatic ring containing carbon or oxygen, said nitrogen heterocyclic rings being unsubstituted, monosubstituted or disubstituted with alkyl groups of from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and iso-propyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperidininum, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like.

The modified peptides of the present invention possess one or more asymmetric carbon atoms and each center may exist in the R or S atom. The present invention contemplates all enantiomeric and epimeric forms as well as the appropriate mixtures thereof as falling within the scope of the invention.

The present invention also includes novel compounds useful as intermediates in the manufacture of the modified tripeptides. Novel dipeptides fall within the compounds of formula I and include:

(S)-N-[4-methyl-2[[(phenylmethoxy)carbonyl]amino]pentyl]glycine, 1,1-dimethylethyl ester;
(S)-N-(2-amino-4-methylpentyl)glycine, 1,1-dimethylethyl ester;
[S-(R*,R*)]-N,N-bis[4-methyl-2-[[(phenylmethoxy)carbonyl]amino]pentyl]glycine, 1,1-dimethylethyl ester;
(S)-N-[1,1-dimethylethoxy)carbonyl]-N-[4-methyl-2-[[phenylmethoxy)carbonyl]amino]pentyl]glycine, 1,1-dimethylethyl ester;
[S-(R*,R*)]-2-[[1-carboxy-3-methylbutyl)amino]methyl]-1-pyrrolidinecarboxylic acid, phenylmethyl ester hydrochloride;
(S)-[[4-methyl-2[[(phenylmethoxy)]carbonyl]amino]pentyl]oxyacetic acid;
(S)-phenylmethyl-[1-[(2-amino-2-oxoethoxy)methyl]-3-methylbutyl]carbamate;
±-[3-phenyl-2-[[(phenylmethoxy)carbonyl]amino]prop]oxyacetic acid;
±-phenylmethyl[1-[(2-amino-2-oxoethoxy)methyl]-2-phenylethyl]-carbamate; (2S)-phenylmethyl2-[(1-carboxy-3-methylbutoxy)methyl]-1-pyrrolidinecarboxylate;
(S)-phenylmethyl2-[(carboxymethoxy)methyl]-1-pyrrolidinecarboxylate, and
(S)-1,1-dimethylethyl[(2-amino-4-methylpentylthio)acetate.

Another important novel intermediate of the present invention is (S)-2-amino-4-methyl-1-pentanethiol.

The modified peptides of the present invention may be prepared by a variety of methods known in the peptide field. Several alternative approaches are described and illustrated below. These approaches are not intended to be exhaustive.

Thus, for example, the following flow chart illustrates the preparation of certain modified peptides of the instant invention.

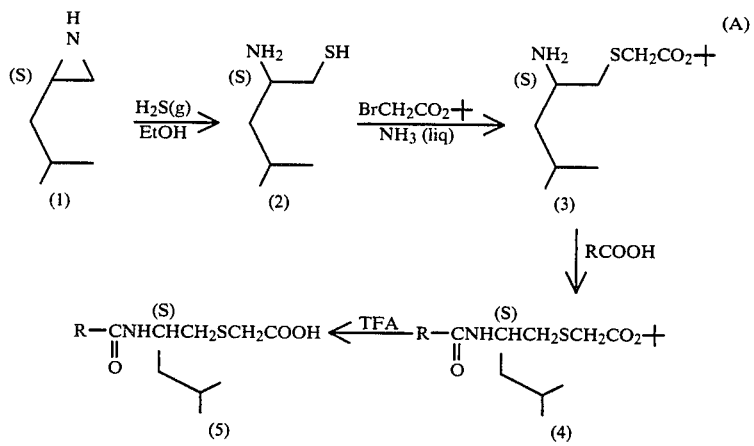

(S)-2-(2-Methylpropyl)-aziridine (1), prepared as described in Bulletin of the Chemical Society of Japan, 35, 1004-10 (1962), is reacted with hydrogen sulfide at −78° C. in ethanol to give (S)-2-amino-4-methyl-1-pentanethiol (2) which is then reacted with tertiary-butylbromoacetate in liquid ammonia to give compound (3). Compound (3) may be condensed with an amino acid as defined above, 2-nicotinic acid or 5-methyl-2-thiophenecarboxylic acid in the presence of a condensation promoting agent, such as N,N-dicyclohexylcarbodiimide or with a reactive derivative of any of the above acids, such as their corresponding acid halides, e.g., chlorides or bromides, or anhydrides. The tertiary butyl ester group in the resulting compound (4) may then be removed by treatment with trifluoroacetic acid. If resulting compound (5) contains further amino protecting groups, they may be removed by methods known in the art, such as hydrolysis or hydrogenolysis. Compound (5) as a free acid may be further converted by methods known per se to corresponding esters and amides as defined above.

A second method for preparing certain modified peptides of the instant invention is illustrated in flow chart B.

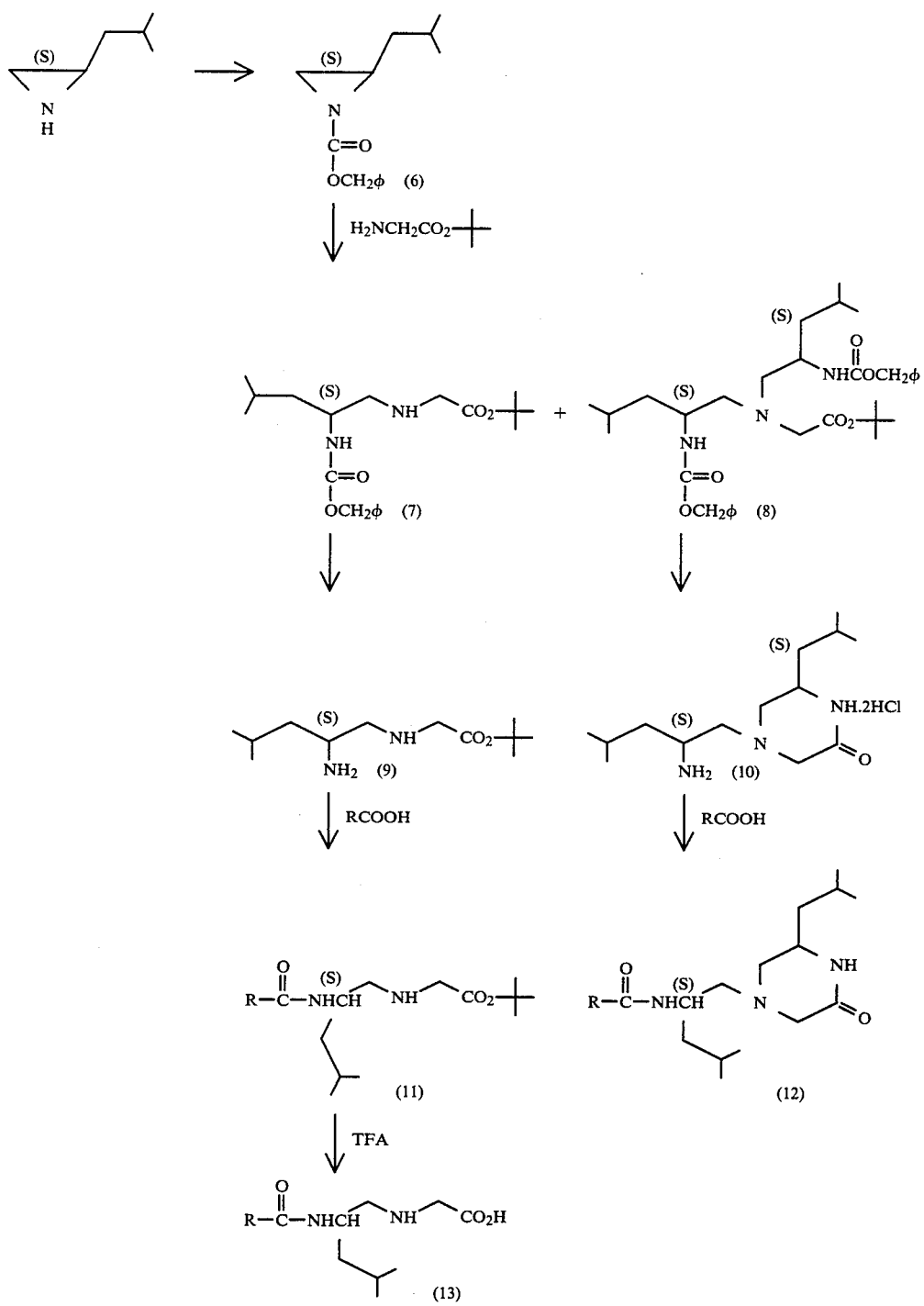

(S)-2-(2-Methylpropyl)-aziridine (1) is protected by a benzyloxycarbonyl group, then reacted with glycine t-butyl ester at reflux temperatures in absolute ethanol to yield products (7) and (8) which are separated by crystallization techniques or column chromatography. Hydrogenolysis of compound (7) with hydrogen in the presence of palladium on carbon removes the benzyloxycarbonyl group. Resulting compound (9) may be condensed with any amino acid above defined, 2-nicotinic or 5-methyl-2-thiophenecarboxylic acid or reactive derivatives thereof in a manner described above. The resulting free acids (13) may also be converted to esters or amides after removal of the tertiary-butoxycarbonyl group with trifluoroacetic acid.

Hydrogenolysis of compound (8) as described above affords a ring-closed compound (10) which may be condensed with the acids already described in like manner to produce the desired products (12) of the instant invention.

Certain modified peptides of the instant invention may be prepared by a third method comprising reacting an alcohol derived from an amino acid as defined above with an α-haloacetyl halide, preferably bromo or chloro, or an α-haloalkanoyl halide, wherein said alkyl is derived from the side chain of an α-aminoalkanoic acid, e.g., leucine, in the presence of sodium acetate. The resulting amide containing both a hydroxyl group and halo atom may be ring-closed with sodium hydride to form a 3-morpholinone derivative which, in turn, may be ring opened by acid hydrolysis, e.g. aqueous hydrochloric acid, to form a modified dipeptide hydrochloride which sole amino group may be protected by, for example, a carbobenzyloxy group and further condensed with an amino acid, e.g. glycine, in the presence of dicyclohexylcarbodiimide and 1-hydroxybenztriazole. The following flow chart C illustrates this approach by way of example in preparing Pro-[CH2O]-Leu-Gly.

sulting Schiff base is reduced with sodium cyanoborohydride.

A sixth method for the preparation of certain modified peptides of the instant invention comprises reacting an alcohol derived from an amino acid whose amino group is protected, 2-nicotinoic acid or 5-methyl-2-thiophenecarboxylic acid with thioacetic acid in the presence of triphenylphosphine and diisopropyl azodicarboxylate to form the corresponding mercapto acetate which is treated with hydrazine hydrate to produce the mercaptan. The mercaptan is reacted with an α-halo, preferably bromo, acetic acid or an α-halocarboxylic acid derived from an amino acid such as, for example, lysine or leucine, in the presence of sodium hydride. Removal of the amino protecting groups affords the desired product.

A seventh method for preparing certain modified

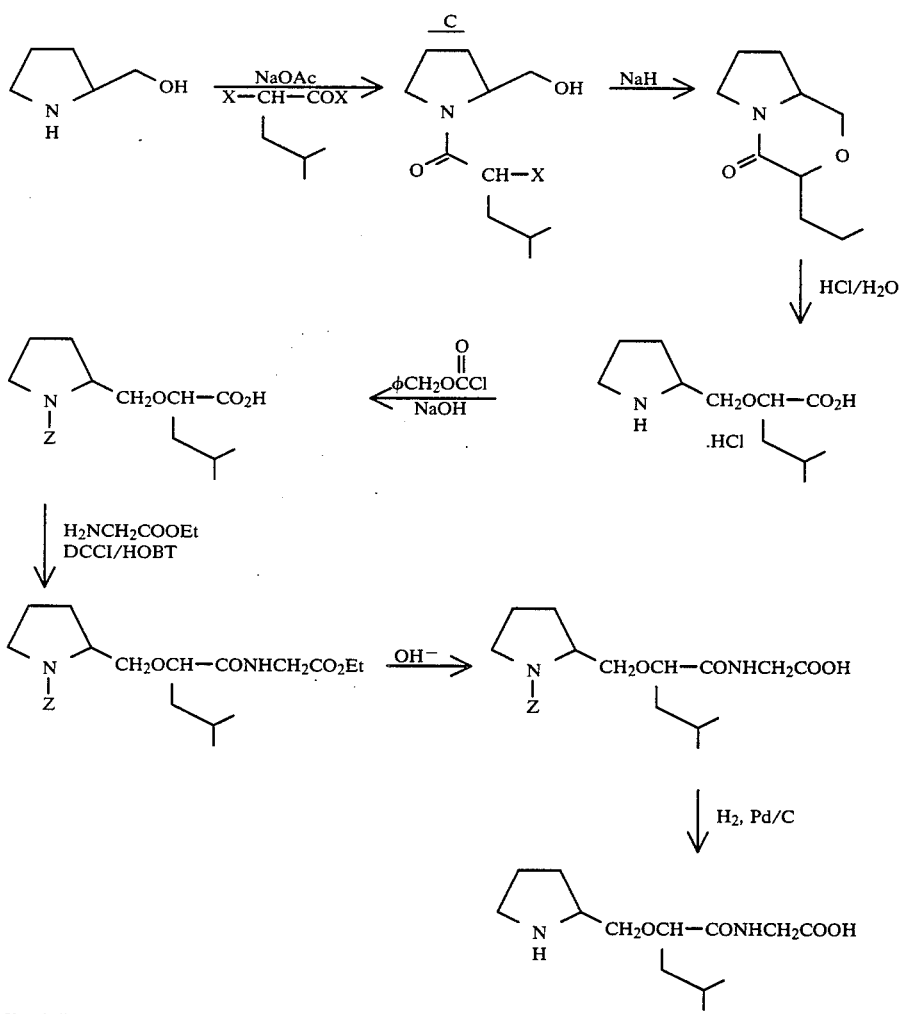

X = halide
Z = carbobenzoxy
DCCI = dicyclohexylcarbodiimide

A fifth method for the preparation of certain modified peptides of the instant invention comprises first the preparation of a dipeptide containing any two of the amino acids defined above according to known methods; removing any blocking group on the terminal amino group and condensing the dipeptide with an aldehyde derived from a third amino acid, 2-nicotinoic acid or 5-methyl-2-thiophene carboxylic acid. The repeptides containing —CH=CH— as the isostere comprises first the condensation of an amino blocked aldehyde of an amino acid with the ylide, 1-trimethylsilylpropyne-3-triphenylphosphonium bromide in the presence of a base such as an alkyllithium compound or sodium hexamethyldisilazide. The resulting product is treated with a borane complex made from cyclohexene and diborane, then hydrolyzed with base and hydrogen peroxide to give the product of the formula

A—CH=CH—CH$_2$CO$_2$H wherein A is the residue of an α-amino acid bonded to the carbon which comprised the aldehyde group of the starting aldehyde of the amino acid used. This acid is then converted to an amide by known means, and, if desired, deblocking the amino acid end of the product for further coupling with other amino acids. The following flow chart D illustrates this series of reactions by way of example in preparing Z-Pro-Leu-[CH=CH]-Gly.

pounds is determined by the test designed to show the compound's ability to reverse amnesia produced by electroconvulsive shock. The test is more fully described in U.S. Pat. No. 4,145,347, issued Mar. 20, 1979, the disclosure of which is herein incorporated by reference. The only deviation in the present instance is that the compounds tested are administered orally, and the duration of the electroconvulsive shock administered is 1.0 seconds.

Employing this test, the following criteria are used in interpreting the percent of amnesia reversal scores: 40 percent or more amnesia reversal (active=A), 25 to 39 percent amnesia reversal (borderline activity=C), and 0 to 25 percent amnesia reversal (inactive=N).

The Table below illustrates amnesia reversal of hex-

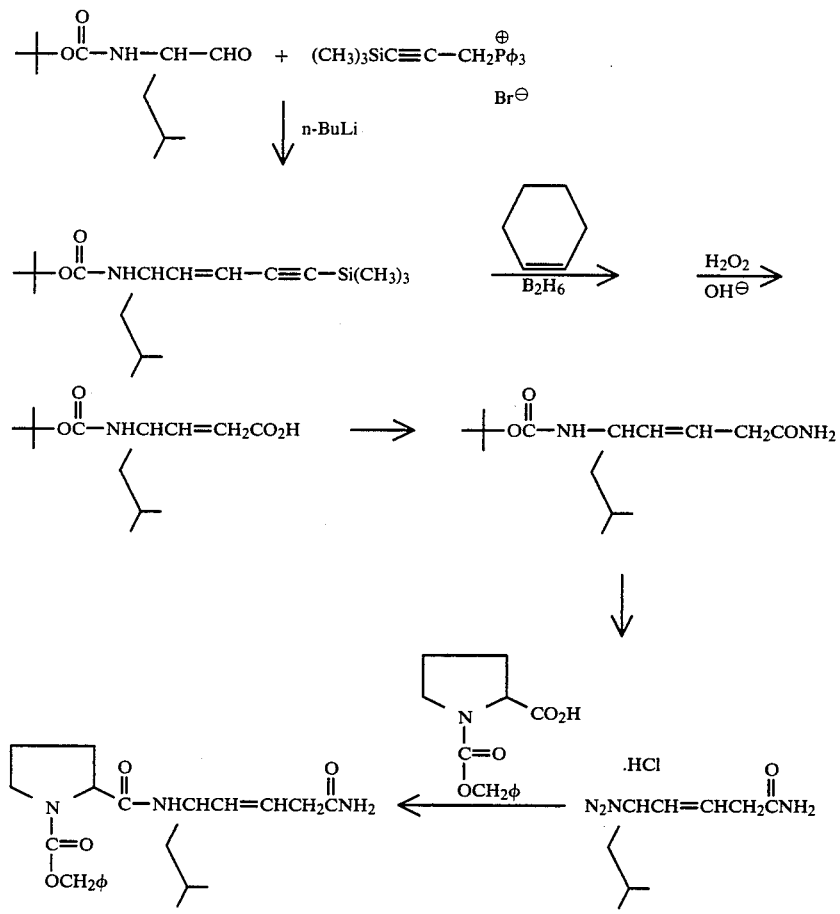

φ = phenyl

The modified peptides in accordance with this invention are effective in treating senility, in enhancing memory, or of reversing the effects of electroconvulsive shock-induced amnesia. The effectiveness of these compounds ahydro-3,5-dioxo-1H-pyrrolizine-2-carboxylic acid ethyl ester when administered to standard experimental laboratory animals in the above referenced test.

TABLE

| Compound | Dose (mg/kg) IM | % Amnesia Reversal Rats | Dose (mg/kg) IM | PO | % Amnesia Reversal Mice |
|---|---|---|---|---|---|
| Z—Pro—Leu—[CH$_2$S]—Gly | 0.100 | 14 (N) | 10.0 | | 69 (A) |
| | 0.010 | 57 (A) | 1.0 | | 77 (A) |
| | 0.001 | 57 (N) | 0.1 | | 69 (A) |
| Z—Pro—Phe—[CH$_2$O]—Gly—NH$_2$ | 0.100 | 0 (N) | | 100 | 71 (A) |
| | 0.010 | 0 (N) | | 10 | 59 (A) |
| | 0.001 | 11 (N) | | 1 | 20 (N) |
| Z—Pro—[CH$_2$NH]—Leu—Gly—NH$_2$ | 0.100 | 0 (N) | | 100 | 57 (A) |

TABLE-continued

| Compound | Dose (mg/kg) IM | % Amnesia Reversal Rats | Dose (mg/kg) IM | Dose (mg/kg) PO | % Amnesia Reversal Mice |
|---|---|---|---|---|---|
| | 0.010 | 0 (N) | | 10 | 67 (A) |
| | 0.001 | 11 (N) | | 1 | 85 (A) |
| 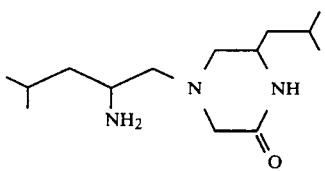 | | | 10.0 | | 29 (C) |
| | | | 1.0 | | 90 (A) |
| | | | 0.1 | | 82 (A) |
| Z—4-Keto—Pro—Leu—[CH₂S]—Gly | 0.100 | 83 (A) | | | |
| | 0.010 | 50 (A) | | | |
| | 0.001 | 17 (N) | | | |
| Z—3-Keto—Pro—Leu—[CH₂S]—Gly | 0.100 | 0 (N) | | | |
| | 0.010 | 0 (N) | | | |
| | 0.001 | 33 (C) | | | |
| Z—Pro—Leu—[CH₂NH]—Gly—NH₂ | 0.100 | 43 (A) | | | |
| | 0.010 | 43 (A) | | | |
| | 0.001 | 43 (A) | | | |
| 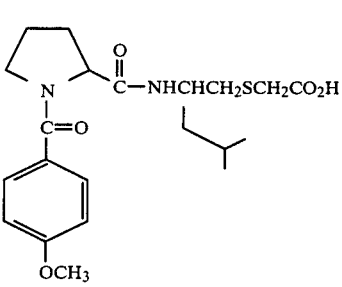 or p-MeO—O—C(=O)—Pro—Leu—[CH₂S]—Gly | 0.100 | 60 (A) | | | |
| | 0.010 | 0 (N) | | | |
| | 0.001 | 40 (A) | | | |
| 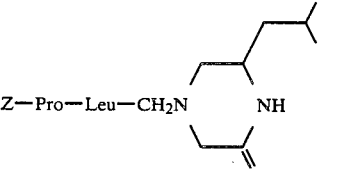 Z—Pro—Leu—CH₂N(NH)... | 0.100 | 50 (A) | | | |
| | 0.010 | 17 (N) | | | |
| | 0.001 | 17 (N) | | | |
| Tos—Pro—[CH₂NH]—D—Leu—Gly—NH₂ | 0.100 | 34 (C) | | | |
| | 0.010 | 0 (N) | | | |
| | 0.001 | 0 (N) | | | |

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as cognition activators, the mammalian dosage range for a 70 kg subject is from 1 to 1500 mg/kg of body weight per day or preferably 25 to 70 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

To enable one skilled in the art to practice the present invention, the following illustrative examples are provided. These examples should not be viewed, however, as limiting the scope of the present invention as defined by the appended claims, but as merely illustrative thereof.

EXAMPLE 1

(S)-2-Amino-4-methyl-1-pentanethiol 8.99 g (0.09 mol) of (S)-2-(2-methylpropyl)aziridine (Bulletin of the Chemical Society of Japan, Vol. 35, pages 1004–1010, 1962) is added in small portions to a solution of 27 g (0.79 mol) hydrogen sulfide in 100 ml absolute ethanol at $-78°$ C. The solution is stirred as it slowly warms to room temperature. The solvent is removed on the rotary evaporator to give a light yellow liquid which crystallizes. The solid is chromatographed on 230–400 mesh silica gel, eluting with dichloromethane followed by 3% methanol in dichloromethane. One obtains 6.63 g of (S)-2-amino-4-methyl-1-pentanethiol; $[\alpha]_D^{25} + 35.5°$ (c 1.02, methanol).

Anal. Calcd for $C_6H_{15}NS$: C, 54.08; H, 11.35, N, 10.51; S. 24.06. Found: C, 53.77; H, 11.20; N, 10.32; S, 24.20.

EXAMPLE 2

(S)-1,1-Dimethylethyl[(2-amino-4-methylpentyl)thio]acetate 2.66 g (0.20 mol) of (S)-2-(2-amino-4-methyl-1-pentanethiol is added to 200 ml liquid ammonia. 3.95 g (0.20 mol) tertiary butyl bromo acetate is added in portions and the solution is stirred until most of the liquid ammonia has evaporated. Water is added to the reaction mixture and is then extracted with ether. The ether layer is dried over magnesium sulfate, filtered, and concentrated to a liquid. The liquid is chromatographed on 230–400 mesh silica gel, eluting with dichloromethane followed by 2% methanol in dichloromethane. One obtains 2.11 g of (S)-1,1-dimethylethyl[(2-amino-4-methylpentyl)thio]-acetate; $[\alpha]_D^{25} + 46.7°$ (c 0.95, methanol).

Anal. calcd for $C_{12}H_{25}NO_2S$: C, 58.26; H, 10.19; N, 5.66; S, 12.96. Found: C, 58.05; H, 9.85; N, 5.55; S, 12.85.

EXAMPLE 3

[S-(R*,R*)]-Phenylmethyl2-[[[1-[[[2-(1,1-dimethylethoxy)-2-oxoethyl]thio]methyl]-3-methylbutyl]amino]-carbonyl]-1-pyrrolidinecarboxylate 7.51 g (0.03 mol) of (S)-1,1-dimethylethyl ester, [(2-amino-4-methylpentyl)thio]-acetic acid, 7.61 g (0.03 mol) carbobenzyloxy-L-proline, and 4.08 g (0.03 mol) 1-hydroxybenzotriazole are dissolved in 100 ml dichloromethane. The solution is cooled to 0° C. and 6.34 g (0.03 mol) of N,N-dicyclohexylcarbodiimide is added all at once. The reaction is kept at 0° C. for three days. The reaction mixture is filtered and the filtrate concentrated on a rotary evaporator. The residue is dissolved in ether, washed with 10% aqueous citric acid solution. The ether solution is dried over magnesium sulfate, filtered, and concentrated to a white solid. The solid is chromatographed on 230–400 mesh silica gel, eluting with dichloromethane followed by 3% methanol in dichloromethane. One obtains 10.99 g of [S-(R*,R*)]-phenylmethyl-2-[[[1-[[[2-(1,1-dimethylethoxy)-2-oxoethyl]thio]methyl]-3-methylbutyl]amino]carbonyl]-1-pyrrolidinecarboxylate; $[\alpha]_D^{25}$ −11.6° (c 1.21, methanol).

Anal. Calcd for $C_{25}H_{38}N_2O_5S$: C, 62.73; H, 8.00; N, 5.85, S, 6.70. Found: C, 63.01; H, 7.79; N, 5.84; S, 6.91.

EXAMPLE 4

[2S-(R*,R*)]-Phenylmethyl2-[[[1-[[(carboxymethyl)thio]methyl]-3-methylbutyl]amino]carbonyl]-1-pyrrolidinecarboxylate To 10 ml of trifluoroacetic acid at 0° C. is added 1.80 g (0.004 mol) of [S-(R*,R*)]-phenylmethyl2-[[[1-[[[2-(1-[[[2-(1,1-dimethylethoxy)-2-oxoethyl]thio]methyl]-3-methylbutyl]amino]carbonyl]-1-pyrrolidine carboxylate. The reaction mixture is allowed to slowly warm to room temperature. The trifluoroacetic acid is removed on the rotary evaporator at 50° C. Ether is thrice added to the residue and stripped off each time. The residual oil is chromatographed on 230–400 mesh silica gel, eluting with dichloromethane followed by 2% methanol in dichloromethane. One obtains 0.92 g of [2S-(R*,R*)-phenylmethyl2-[[[1-[[(carboxymethyl)thio]methyl]-3-methylbutyl]amino]carbonyl]-1-pyrrolidinecarboxylate; $[\alpha]_D^{25}$ −18.0° (c 0.92, methanol).

Anal. Calcd for $C_{21}H_{30}N_2O_5S.1/10CH_2Cl_2$: C, 58.80; H, 7.06; N, 6.50; S, 7.44. Found: C, 58.83; H, 7.07; N, 6.40; S, 7.71.

EXAMPLE 5

[S-(R*,R*)]-Phenylmethyl 2-[[[1-[[(2-amino-2-oxoethyl)thio]methyl]-3-methylbutyl]amino]carbonyl]-1-pyrrolidinecarboxylate [4.59 g (0.010 mol) of [2S-R*,R*)]-phenylmethyl 2-[[[1-[[(carboxymethyl)thio]methyl]-3-methylbutyl]amino]carbonyl]-1-pyrrolidinecarboxylate is dissolved in 100 ml dichloromethane and the solution is cooled to −5° C. 0.99 g of methylchloroformate (0.010 mol) is added and the solution stirred for ten minutes. Then 1.10 g (0.01 mol) triethylamine is added and the solution cooled to −15° C. Ammonia gas is bubbled into the solution for one hour. The solution is then kept at room temperature for three days. The reaction mixture is filtered, the filtrate washed with saturated aqueous sodium hydrogen carbonate solution and 10% aqueous citric acid solution. The organic layer is dried over magnesium sulfate, filtered, and concentrated to a clear oil. The oil is chromatographed on 230–400 mesh silica gel, using dichloromethane followed by 2% methanol in dichloromethane as eluant. One obtains 0.92 g [S-(R*,R*)]-phenylmethyl 2-[[[1-[[(2-amino-2-oxoethyl)thio]methyl]-3-methylbutyl]amino]carbonyl]-1-pyrrolidinecarboxylate; $[\alpha]_D^{25}$ −30.3° (c 1.12, methanol).

Anal. Calcd for $C_{21}H_3,N_3O_4S.1/2H_2O$: C, 58.58; H, 7.49; N, 9.76; S, 7.45. Found: C, 58.72; H, 7.60; N, 9.67; S, 7.73.

EXAMPLE 6

[S-(R*,R*)]-Phenylmethyl 2-[[[1-[[[2-(1,1-dimethylethoxy)-2-oxoethyl]thio]methyl]-3-methylbutyl]amino]carbonyl]-4-oxo-1-pyrrolidinecarboxylate 4.70 g (0.019 mol) of (S)-1,1-dimethylethyl [(2-amino-4-methylpentyl)thio]acetate, 5.0 g (0.019 mol) (5)-1-phenyl methyl-4-oxo-1,2-pyrrolidinedicarboxylate, 2.57 g (0.019 mol) 1-hydroxybenzotriazole, and 3.93 g (0.019 mol) N,N-dicyclohexylcarbodiimide are reacted according to the procedure for Example 3 to give 3.49 g of [S-(R*,R*)]-phenylmethyl 2-[[[1-[[[2-(1,1-dimethylethoxy)-2]-oxoethyl]thio]methyl]butyl]amino]carbonyl]-4-oxo-1-pyrrolidine carboxylate as a white solid, mp 89°–91°. $[\alpha]_D^{25}$ +33.2° (c 1.06, methanol).

Anal. Calcd for $C_{25}H_{36}N_2O_6S$: C, 60.95; H, 7.37; N, 5.69; S, 6.51. Found: C, 60.99; H, 7.28; N, 5.66; S, 6.79.

EXAMPLE 7

[S-(R*,R*)]-Phenylmethyl 2-[[[1-[[(carboxymethyl)thio]methyl]-3-methylbutyl]amino]carbonyl]-4-oxo-1-pyrrolidinecarboxylate 4.84 g (0.01 mol) [S-(R*,R*)]-phenylmethyl 2-[[[1-[[[2-(1,1-dimethylethoxy)-2-oxoethyl]thio]methyl]-3-methylbutyl]amino]carbonyl]-4-oxo-1-pyrrolidinecarboxylate and 40 ml trifluoroacetic acid are reacted according to the procedure for Example 4 to give 0.82 g of [S-(R*,R*)]-phenylmethyl 2-[[[1-[[(carboxymethyl)-thio]methyl]-3-methylbutyl]amino]carboxymethyl)thio]methyl]-3-methylbutyl]amino]carbonyl]-4-oxo-1-pyrrolidinecarboxylate as a foam. $[\alpha]_D^{25}$ −32.5° (c 1.02, methanol).

Anal. Calcd for $C_{21}H_{28}N_2O_6S$: C, 67.13; H, 6.12; N, 3.40; S, 7.79. Found: C, 66.83; H, 5.95; N, 3.33; S, 8.07.

EXAMPLE 8

(S)-1,1-Dimethylethyl [[4-methyl-2-[[(5-methyl-2-thienyl)carbonyl]amino]pentyl]thio]acetate 3.00 g (0.012 mol) of (S)-1,1-dimethylethyl [(2-amino-4-methylpentyl)thio]acetate, 172 g (0.012 mol) 5-methyl-2-thiophene carboxylic acid, 1.64 g (0.012 mol) 1-hydroxybenzotriazole, and 2.50 g (0.012 mol) N,N-dicyclohexylcarbodiimide are reacted according to the procedure for Example 3 to give 0.64 g of (S)-1,1-dimethylethyl [[4-methyl-2-[[[5-methyl-2-thienyl]carbonyl]amino]pentyl]thio]acetate as a crystalline solid, mp 81°–83°; $[\alpha]_D^{25}$ +56.5° (C 0.63, methanol).

Anal. Calcd for $C_{18}H_{29}NO_3S_2$: C, 58.19; H, 7.87; N, 3.77; S, 17.26. Found: C, 58.31; H, 7.81; N, 3.76; S, 17.31.

EXAMPLE 9

(S)-[[4-Methyl-2-[[(5-methyl-2-thienyl)carbonyl]amino]pentyl]thio]acetic acid 1.83 g (0.005 mol) (S)-1,1-dimethylethyl [[4-methyl-2-[[[5-methyl-2-thienyl]carbonyl]amino]pentyl]thio]acetate and 10 ml trifluoroacetic acid are reacted according to the procedure for Example 4 to give 0.75 g of (S)-[[4-methyl-2-[[(5-methyl-2-thienyl)carbonyl]amino]pentyl]-thio]-acetic acid as a viscous oil. $[\alpha]_D^{25}$ +57.3° (c 0.52, methanol).

Anal. Calcd for $C_{14}H_{21}NO_3S_2$: C, 53.31; H, 6.71; N, 4.44; S, 20.33. Found: C, 53.55; H, 6.81; N, 4.28; S, 20.03.

EXAMPLE 10

[S-(R*,R*)]-Phenylmethyl 5-oxo-[2-[[[1-[[[2-(1,1-dimethylethoxy)-2-oxoethyl]thio]methyl]-3-methyl]butyl]amino]carbonyl]-1-pyrrolidinecarboxylate 2.21 g (0.009 mol) of (S)-1,1-dimethylethyl [(2-amino-4-methylpentyl)thio]acetate, 2.34 g (0.008 mol) N-carbobenzoxy-L-pyroglutamic acid, 1.22 g (0.008 mol) 1-hydroxybenzotriazole, and 1.85 g (0.009 mol) N,N-dicyclohexylcarbodiimide are reacted according to the procedure for Example 3 to give 2.14 g of [S-(R*,R*)]-phenylmethyl 5-oxo-[2-[[[1-[[[2-(1,1-dimethylethoxy)-2-oxoethyl]thio]methyl]-3-methyl]butyl]amino]carbonyl]-1-pyrrolidinecarboxylate as a white solid. $[\alpha]_D^{25} + 13.0°$ (c 1.06, methanol)

Anal. Calcd for $C_{25}H_{36}N_2O_6S$: C, 60.95; H, 7.37; N, 5.69; S, 6.51. Found: C, 61.07; H, 7.62; N, 5.58; S, 6.57.

EXAMPLE 11

[S-(R*,R*)]-1,1-Dimethylethyl [[4-methyl-2-[[(5-oxo-2-pyrrolidinyl)carbonyl]amino]pentyl]thio]acetate 5.0 g (0.020 mol) of (S)-1,1-dimethyl[(2-amino-4-methylpentyl)thio]acetate, 2.86 g (0.022 mol) L-pyroglutamic acid, 3.00 g (0.022 mol) 1-hydroxybenzotriazole, and 4.56 g (0.022 mol) N,N-dicyclohexylcarbodiimide are reacted according to the procedure for Example 3 to give 1.24 g of [S-(R*,R*)]-1,1-dimethylethyl [[4-methyl-2-[[(5-oxo-2-pyrrolidinyl)carbonyl]amino]pentyl]thio]acetate as a light yellow oil.

Anal. Calcd for $C_{17}H_{30}N_2O_4S$: C, 56.96; H, 8.43; N, 7.81; S, 8.94. Found: C, 57.02; H, 8.44; N, 7.68; S, 8.90.

EXAMPLE 12

[S-(R*,R*)]-Phenylmethyl 5-oxo-2-[[[1-[[(carboxymethyl)thio]methyl]-3-methylbutyl]amino]carbonyl]-1-pyrrolidinecarboxylate 1.81 g (0.0037 mol) of [S,(R*,R*)]-phenyl methyl-5-oxo-[2-[[[1-[[[2-(1,1-dimethylethoxy)-2-oxoethyl]thio]methyl]-3-methyl]butyl]amino]carbonyl]-1-pyrrolidinecarboxylate and 10 ml trifluoroacetic acid are reacted according to the procedure for Example 4 to give 0.19 g of [S-(R*,R*)]-phenylmethyl 5-oxo-2-[[[-1-[[(carboxymethyl)thio]methyl]-3-methylbutyl]amino]carbonyl]-1-pyrrolidinecarboxylate as a white solid $[\alpha]_D^{25} - 0.26°$ (c 0.54, methanol).

Anal. Calcd for $C_{21}H_{28}N_2O_6S$: C, 57.78; H, 6.46; N, 6.42; S, 7.34. Found: C, 57.57; H, 6.40; N, 6.31; S, 7.38.

EXAMPLE 13

(S)-1,1-Dimethylethyl-[[4-methyl-2-[(2-pyridinylcarbonyl)amino]pentyl]thio]acetate 3.00 g (0.012 mol) of (S)-1,1-dimethylethyl [(2-amino-4-methylpentyl)thio]acetate, 1.51 g (0.012 mol) 2-picolinic acid, 1.64 g (0.012 mol) 1-hydroxybenzotriazole, and 2.50 g (0.012 mol) N,N-dicyclohexylcarbodiimide are reacted according to the procedure for Example 3 to give 0.37 g of (S)-1,1-dimethylethyl-[[4-methyl-2-[(2-pyriidinylcarbonyl)amino]pentyl]thio]acetate as a clear oil. $[\alpha]_D^{25} + 57.9°$ (C 0.57, methanol).

Anal. Calcd for $C_{18}H_{28}N_2O_3S$: C, 61.33, H, 8.01; N, 7.95; S, 9.10. Found: C, 61.65; H, 7.90; N, 7.86; S, 9.32.

EXAMPLE 14

(S)-[[4-Methyl-2-[(2-pyridinylcarbonyl)amino]pentyl]thio]acetate monohydrochloride 1.68 g (0.0048 mol) (S)-1,1-dimethylethyl-[[4-methyl-2-[(2-pyridinylcarbonyl)amino]pentyl]thio]acetate and 10 ml trifluoroacetic acid are reated two days at room temperature. The trifluoroacetic acid is removed on the rotary evaporator, the residue dissolved in ether, and extracted into 10% aqueous sodium carbonate solution, which is washed with ether. The aqueous solution is made acidic with solid citric acid and is then extracted with methylene chloride. The organic layer is dried over magnesium sulfate, filtered, and concentrated to an oil. The oil is dissolved in ether and hydrogen chloride gas in ether is added. 1.27 g of (S)-[[4-methyl-2-[(2-pyridinylcarbonyl)amino]pentyl]thio]acetate monohydrochloride is obtained. $[\alpha]_D^{25} + 48.3°$ (c 0.60, methanol).

Anal. Calcd for $C_{14}H_{20}N_2O_3S.HCl.1/5H_2O$: C, 49.97; H, 6.41; N, 8.32; S, 9.52. Found: C, 50.05; H, 6.55; N, 7.94; S, 9.30.

EXAMPLE 15

[S-(R*,R*)]-Phenylmethyl 2[[[1-[[[2-(1,1-dimethylethoxy)-2-oxoethyl)sulfonyl]methyl]-3-methylbutyl]amino]carbonyl]-1-pyrrolidinecarboxylate 2.54 g (0.0053 mol) of [S-(R*,R*)]-phenylmethyl 2-[[[1-[[[2-(1,1-dimethylethoxy)-2-oxoethyl]thio]methyl]-3-methylbutyl]amino]carbonyl]-pyrrolidinecarboxylate is mixed with 60 ml chloroform and 1.15 g (0.0067 mol) m-chloroperoxybenzoic acid at room temperature. The solution is refluxed for one hour and 1.15 g (0.0067 mol) more m-chloroperoxybenzoic acid is added and the solution is refluxed overnight. Then 1.15 g (0.0067 mol) more m-chloroperoxybenzoic acid is added and the solution is refluxed three hours. The cooled chloroform solution is washed with 10% aqueous sodium carbonate, dried over magnesium sulfate, filtered and stripped to a white solid. The solid is chromatographed on 230–400 mesh silica gel using dichloromethane, then 2% methanol in dichloroomethane as eluant. One obtains 1.97 g of [S-(R*,R*)]-phenylmethyl 2-[[[-1-[[[2-(1,1-dimethylethoxy)-2-oxoethyl]sulfonyl]methyl]-3-methylbutyl]amino]carbonyl]-1-pyrrolidinecarboxylate as a white solid. $[\alpha]_D^{25} - 38.3°$ (c 1.09, methanol).

Anal. Calcd for $C_{25}H_{38}N_2O_7S$: C, 58.80, H, 7.50; N, 5.47; S, 6.28. Found: C, 58.89; H, 7.24; N, 5.44; S, 6.55.

EXAMPLE 16

[S,(R*,R*)]-2-[[[1-[[(Carboxymethyl)sulfonyl]methyl]-3-methylbutyl]amino]carbonyl]-1-pyrrolidinecarboxylate 1.97 g (0.0039 mol) [S,(R*,R*)]-phenylmethyl 2-[[[1-[[[2-(1,1-dimethylethoxy)-2-oxoethyl]sulfonyl]methyl]-3-methylbutyl]-amino]carbonyl]-1-pyrrolidinecarboxylate is dissolved in 75 ml dichloromethane and 10 ml trifluoroacetic acid is added and the solution stirred overnight at room temperature. The solution is concentrated on the rotary evaporator and the residue chromatographed on 230-400 mesh silica gel using dichloromethane followed by 2% methanol in dichloromethane as eluent. One obtains 0.93 g of [S,(R*,R*)]-2-[[[1-[[(carboxymethyl)sulfonyl]methyl]-3-methylbutyl]amino]carbonyl]-1-pyrrolidinecarboxylate as a white solid.

Anal. Calcd for $C_{21}H_{30}N_2O_7S$: C, 55.49; H, 6.65; N, 6.16; S, 7.05. Found: C, 55.65; H, 6.58; N, 5.89; S, 7.31.

EXAMPLE 17

[S-(R*,R*)]-1,1-Dimethylethyl [[2-[[[1-4-methoxybenzoyl)-2-pyrrolidinyl]carbonyl]amino]-4-methylpentyl]thio]acetate 5.0 g (0.020 mol) (S)-1,1-dimethylethyl[(2-amino-4-methylpentyl)thio]acetate, 5.52 g (0.022 mol) 1-(4-methoxybenzoyl)-L-proline, 3.00 g (0.022 mol) 1-hydroxybenzotriazole, and 4.56 g (0.022 mol) N,N-dicyclohexycarbodiimide are reacted according to the procedure for Example 3 to give 3.48 g of [S-(R*,R*)]-1,1-dimethylethyl [[2-[[[1-4-methoxybenzoyl)-2-pyrrolidinyl]carbonyl]amino]-4-methylpentyl]thio]acetate as a white solid, mp 117°–121° $[\alpha]_D^{25} - 30.0°$ (c 1.14, methanol).

Anal. Calcd for $C_{25}H_{38}N_2O_5S$: C, 62.73; H, 8.00; N, 5.85; S, 6.70. Found: C, 62.97; H, 7.93; N, 5.66; S, 6.51.

EXAMPLE 18

[S-(R*,R*)]-[[2-[[[1-(4-Methoxybenzoyl)-2-pyrrolidinyl]carbonyl]amino]-4-methylpentyl]thio]acetate 4.43 g (0.0093 mol) [S-(R*,R*)]-1,1,dimethyl ethyl-[[2-[[[1-(4-methoxybenzoyl)-2-pyrrolidinyl]carbonyl]amino]-4-methylpentyl]thio]acetate and 18 ml trifluoroacetic acid are reacted according to the procedure for Example 4 to give 3.19 g of [S-(R*,R*)]-[[2-[[[1-(4-methoxybenzoyl)-2-pyrrolidinyl]carbonyl]amine]-4-methoxypentyl]thio]acetate as a white foam $[\alpha]_D^{25} - 38.1°$ (c 0.54, methanol).

Anal. Calcd for $C_{21}H_{30}N_2O_5S$: C, 59.69; H, 7.16; N, 6.63; S, 7.59. Found: C, 59.42; H, 6.93; N, 6.96; S, 7.83.

EXAMPLE 19

(S)-2-(2-Methylpropyl)-1-aziridinecarboxylic acid, phenylmethyl ester

A solution of 24.3 g of (S)-2-(2-methylpropyl)aziridine [Bull. Chem. Soc. (Japan) 35, 1004 (1962).] in 500 ml of ether is treated with 34.2 ml of triethylamine and cooled in ice. While stirring rapidly 40.4 ml (a 10% excess) of benzyl chloroformate is added dropwise over a 30 minute period. After stirring for one hour at 0°, the triethylamine, hydrochloride is filtered off and the ether removed under reduced pressure. The residue is distilled under reduced pressure. After a forerun of benzyl chloride, the product distills at 105°–122°/0.6 mm. There is obtained 51.66 g (90.5% yield) of (S)-2-(2-methylpropyl)-1-aziridinecarboxylic acid, phenylmethyl ester.

EXAMPLE 20

[S-(R*,R*)]-N,N-Bis[4-methyl-2-[[(phenylmethoxy)carbonyl]amino]pentyl]glycine, 1,1-dimethylethyl ester A refluxing solution of 15.1 g (a 10% excess) of glycine t-butyl ester in 200 ml of absolute ethanol is treated dropwise over one hour with a solution of 24.2 g of (S)-2-(2-methylpropyl)-1-aziridinecarboxylic acid, phenylmethyl ester in 50 ml of absolute ethanol. The refluxing is continued over two nights. The solvent is removed under reduced pressure and the residue chromatographed on 1.5 kg of silica gel, eluting with chloroform/ethylacetate (3:1). Combining the fractions containing the faster eluting compound gives 14.3 g of an oil which crystallizes on standing. A small example, recrystallized from hexane has mp 107°–108°, $[\alpha]_D^{23} - 16.3°$ (c 1.03, methanol). Spectral and elemental analysis shows this to be [S-(R*,R*)]-N,N-bis[4-methyl-2-[[(phenylmethoxy)carbonyl]amino]pentyl]glycine, 1,1-dimethylethyl ester.

Combining the fractions containing the slower eluting compounds gives 17.6 g of an oil which crystallizes on standing, mp 50°–52°, $[\alpha]_D^{23} - 10.0°$ (c 1.0, methanol). Spectral and elemental analysis shows this to be (S)-N-[4-methyl-2-[[(phenylmethoxy)carbonyl]amino]pentyl]glycine, 1,1-dimethylethyl ester.

EXAMPLE 21

(S)-N-(2-Amino-4-methylpentyl)glycine, 1,1-dimethylethyl ester

A solution of 17.43 g of (S)-N-[4-methyl-2-[[(phenylmethoxy)carbonyl]amino]pentyl]glycine, 1,1-dimethylethyl ester in 150 ml of methanol is reduced at 25°, 50 psi using 1 g of 20% palladium on carbon as the catalyst. The filtered solution is treated with 7.84 g of phosphorous acid in 10 ml of ether and the solvent removed under reduced pressure. The residue is partitioned between ether and 10% sodium hydroxide. The aqueous phase is washed five times with ether and the combined ether washes are washed with saturated sodium chloride solution and dried over magnesium sulfate. Removal of the solvent under reduced pressure at 25° gives 10.28 g of crude (S)-N-(2-amino-4-methylpentyl)-glycine, 1,1-dimethylethyl ester. The crude product is sufficiently pure for use in subsequent reactions.

EXAMPLE 22

[S-(R*,R*)]-2-[[[1-[[[2-(1,1-Dimethylethoxy)-2-oxoethyl]amino]methyl]-3-methylbutyl]amino]carbonyl]-1-pyrrolidinecarboxylic acid, phenylmethyl ester A solution of 1.34 g of (S)-N-(2-amino-4-methylpentyl)glycine, 1,1-dimethylethyl ester, 1.45 g of Z-proline, and 786 mg of hydroxybenzotriazole hydrate in 40 ml of tetrahydrofuran is cooled in ice and treated dropwise with a solution of 1.21 g of N,N'-dicyclohexylcarbodiimide in 10 ml of tetrahydrofuran. After one hour at 0°, the solution is allowed to stir at room temperature overnight. The solution is then filtered and the filtrate concentrated under reduced pressure. The residue is taken up in ethyl acetate, washed two times with saturated sodium bicarbonate, then with saturated sodium chloride. After drying over magnesium sulfate, the solvent is removed under reduced pressure. The residue is chromatographed on 145 g of silica gel, eluting with chloroform/methanol, (98:2). Combining the appropriate fraction and removing the solvent under reduced pressure gives 1.77 g of [S-(R*,R*)]-2-[[[1-[[[2-(1,1-dimethylethoxy)-2-oxoethyl]amino]methyl]-3-methylbutyl]amino]carbonyl]-1-pyrrolidinecarboxylic acid, phenylmethyl ester.

EXAMPLE 23

[S-(R*,R*)]-2-[[[1-[[(2-Methoxy-2-oxoethyl)amino]methyl]-3-methylbutyl]amino]carbonyl]-1-pyrrolidinecarboxylic acid, phenylmethyl ester To 50 ml of methanol, saturated with hydrogen chloride gas is added 1.77 g of [S-(R*,R*)]-2-[[[1-[[[-2-(1,1-dimethylethoxy)-2-oxoethyl]amino]methyl]-3-methylbutyl]amino]carbonyl]-1-pyrrolidinecarboxylic acid, phenylmethyl ester in 10 ml of methanol. After standing at room temperature for four hours, the solution is kept at 0° overnight. The solvent is then removed under reduced pressure and the residue taken up in ethyl acetate. The ethyl acetate solution is washed two times with saturated sodium bicarbonate solution, once with saturated sodium chloride solution, and then dried over magnesium sulfate. Removal of the solvent under reduced pressure gives 1.14 g of [S-(R*,R*)]-2-[[[1-[[(2-methoxy-2-oxoethyl)amino]methyl]-3-methylbutyl]amino]carbonyl]-1-pyrrolidinecarboxylic acid, phenylmethyl ester.

EXAMPLE 24

[S-(R*,R*)]-2-[[[1-[[(2-Amino-2-oxoethyl)-amino]methyl]-3-methylbutyl]amino]-carbonyl]-1-pyrrolidinecarboxylic acid, phenylmethyl ester, monohydrochloride A solution of 2.4 g of [S-(R*,R*)]-2-[[[1-[[(2-methoxy-2-oxoethyl)amino]methyl]-3-methylbutyl]amino]carbonyl]-1-pyrrolidinecarboxylic acid, phenylmethyl ester in 100 ml of methanol is cooled in ice and treated with ammonia gas for 15 minutes. The flask is then stoppered and allowed to stir at room temperature overnight. The solvent is then removed under reduced pressure and the residue chromatographed on 190 g of silica gel eluting with chloroform/methanol, (9:1). The appropriate fractions are combined giving 1.62 g of an oil. This is taken up in chloroform and treated dropwise with a solution of hydrogen chloride gas in ether. The solution is decanted from the resulting gum, and the gum is triturated with ether. Collecting the resulting solid and washing with ether gives 1.1 g of [S-(R*,R*)]-2-[[[1-[[(2-amino-2-oxoethyl)-amino]methyl]-3-methylbutyl]amino]carbonyl]-1-pyrrolidinecarboxylic acid, phenylmethyl ester, monohydrochloride, as an amorphous solid, mp 75°–95° eff., $[\alpha]_D^{23} -55.2°$ (c 1.16, methanol).

EXAMPLE 25

[S-(R*,R*)]-N-[4-Methyl-2-[[(5-oxo-2-pyrrolidinyl)carbonyl]amino]pentyl]glycine, 1,1-dimethylethyl ester A solution of 1.54 g of (S)-N-(2-amino-4-methylpentyl)glycine, 1,1-dimethylethyl ester, 890 mg of L-pyroglutamic acid, and 904 mg of hydroxybenzotriazole, hydrate in 30 ml of N,N-dimethylformamide is cooled in ice and treated dropwise with a solution of 1.4 g of N,N'-dicyclohexylcarbodiimide in 5 ml of N,N-dimethylformamide. After stirring at 0° for 0.5 hours, the mixture is kept at room temperature overnight. The mixture is filtered and the solvent distilled off under high vacuum. The residue is taken up in ethyl acetate and the ethyl acetate washed two times with water. The water is adjusted to pH 6 and lyophilized. The residue is chromatographed on 95 g of silica gel eluting with chloroform/methanol, (94:6). Combining the appropriate fractions gives 1.2 g of [S-(R*,R*)]-N-[4-methyl-2-[[(5-oxo-2-pyrrolidinyl)carbonyl)amino]pentyl]glycine, 1,1-dimethylethyl ester. The product is homogeneous by thin layer chromatography.

EXAMPLE 26

[S-(R*,R*)]-N-[4-Methyl-2-[[(5-oxo-2-pyrrolidinyl)carbonyl]amino]pentyl]glycine, monohydrochloride A solution of 1.2 g of [S-(R*,R*)]-N-[4-methyl-2-[[(5-oxo-2-pyrrolidinyl)carbonyl]amino]pentyl]glycine, 1,1-dimethylethyl ester in 15 ml of trifluoroacetic acid is kept at room temperature for two hours. The solvent is removed under reduced pressure and the residue dissolved in dichloromethane and the solvent again removed under reduced pressure. The residue is then taken up in dichloromethane and treated dropwise with a solution of hydrogen chloride gas in ether. The solvent is removed under reduced pressure, and the residue triturated with ether. Collecting the solid and washing with ether gives 730 mg of [S-(R*,R*)]-N-[4-methyl-2-[[(5-oxo-2-pyrrolidinyl)carbonyl]amino]pentyl]glycine, monohydrochloride as an amorphous solid, mp 94°–125° eff., $[\alpha]_D^{23} -4.3°$ (c 1.1, methanol).

EXAMPLE 27

[S-(R*,R*)]-4-(2-Amino-4-methylpentyl)-6-(2-methylpropyl)-2-piperazone, dihydrochloride.

A solution of 8.15 g of [S-(R*,R*)]-N,N-bis[4-methyl-2-[[(phenylmethoxy)carbonyl]amino]pentyl]glycine, 1,1-dimethyl ester in 100 ml of methanol is reduced at 24°, 50 psi using 0.5 g of 20% palladium on carbon as the catalyst. The catalyst is filtered off the solvent removed under reduced pressure. The residue is taken up in 125 ml of methanol and heated at reflux for five hours. Removing the solvent under reduced pressure gives 4.13 g of an oil homogeneous by thin layer. This material is used in the following reaction.

The dihydrochloride is prepared by taking the free base up in ether and adding dropwise a solution of hydrogen chloride gas in ether. The precipitated product is collected and washed with ether giving [S-(R*,R*)]-4-(2-amino-4-methylpentyl)-6-(2-methylpropyl)-2-piperazone, dihydrochloride as an amorphous solid, mp 163°–173°. The structure is confirmed by spectral and elemental analysis. The compound is homogeneous by thin layer chromatography.

EXAMPLE 28

[2S-[2R*,4[R*(R*)]]]-2-[[[3-Methyl-1-[[3-(2-methylpropyl)-5-oxo-1-piperazinyl]methyl]butyl]amino]carbonyl]-1-pyrrolidinecarboxylic acid, phenylmethyl ester, monohydrochloride.

A solution of 2.0 g of [S-(R*,R*)]-4-(2-amino-4-methylpentyl)-6-(2-methylpropyl)-2-piperazone, 1.95 g of Z-proline, and 1.05 g of hydroxybenzotriazole hydrate in 40 ml of tetrahydrofuran is cooled in ice and treated dropwise with a solution of 1.63 g of N,N'-dicyclohexylcarbodiimide in 5 ml of tetrahydrofuran. After 0.5 hour at 0°, the mixture is kept at room temperature overnight. The mixture is filtered and the solvent removed under reduced pressure. The residue is taken up in ethyl acetate and washed successively with water, saturated sodium bicarbonate, and then saturated sodium chloride. Drying over magnesium sulfate and removal of the solvent under reduced pressure gives a gum. This is chromatographed on 190 g of silica gel, eluting with chloroform/methanol, (95:5). The appropriate fractions are combined and the residue taken up in ether and treated with hydrogen chloride gas in ether. The solid is collected and washed with ether giving 1.69 g of [2S-[2R*,4[R*(R*)]]]-2-[[[3-methyl-1-[[3-(2-methylpropyl)-5-oxo-1-piperazinyl]methyl]butyl]amino]carbonyl]-1-pyrrolidinecarboxylic acid, phenylmethyl ester, monohydrochloride as an amorphous solid, mp 95°–120°, $[\alpha]_D^{23} -25.5°$ (c 1.05, methanol). The compound is homogeneous by thin layer chromatography.

EXAMPLE 29

[2S-[2R*,4[R*(R*)]]]-N-[3-Methyl-1-[[3-(2-methylpropyl)-5-oxo-1-piperazinyl]methyl]butyl]-5-oxo-2-pyrrolidinecarboxamide, monohydrochloride A solution of 2.13 g of [S-(R*,R*)]-4-(2-amino-4-methylpentyl)-6-(2-methylpropyl)-2-piperazone, 1.08 g of L-pyroglutamic acid, and 1.13 g of hydroxybenzotriazole hydrate in 25 ml of N,N-dimethylformamide is cooled in ice and treated dropwise with 1.74 g of N,N'-dicyclohexylcarbodiimide in 5 ml of N,N-dimethylformamide. After one hour at 0°, the mixture is left at room temperature overnight. The mixture is filtered and the solvent is distilled off under high vacuum. The residue is taken up in ethyl acetate and washed twice with water. The water washes are adjusted to pH 7.2 and lyophilized. The residue is chromatographed on 175 g of silica gel, eluting with chloroform/methanol, (9:1). The appropriate fractions are combined. The residue is taken up in chloroform and treated with hydrogen chloride gas in ether. The solid is collected and triturated with additional ether. There is obtained 0.9 g of [2S-[2R*,4[R*(R*)]]]-N-[3-methyl-1-[[3-(2-methylpropyl)-5-oxo-1-piperazinyl]methyl]butyl]-5-oxo-2-pyrrolidinecarboxamide, monohydrochloride as an amorphous solid, mp 77°–110°, $[\alpha]_D^{23} -21.3°$ (c 1.03, methanol). The product is homogeneous by thin layer chromatography.

EXAMPLE 30

(S)-2-Chloro-N-[1-(hydroxymethyl)-3-methylbutyl]acetamide

A solution of chloroacetyl chloride, 25.64 g (0.227 mol), in 57 ml of acetone is added dropwise with stirring to a solution of L-leucinol, 26.63 g (0.227 mol), and sodium acetate, 37.24 g (0.454 mol), in a mixture of 340 ml of acetone and 170 ml of water at 0°–5° C. The mixture is stirred and allowed to reach room temperature over two hours, the solvent is evaporated in vacuo and the residue is suspended in 250 ml of chloroform and washed with water, 2×300 ml. The chloroform layer is separated, dried over sodium sulfate, evaporated in vacuo and the residue is purified by chromatography using silica gel and eluting with dichloromethane-methanol (95:5) to give (S)-2-chloro-N-[1-(hydroxymethyl)-3-methylbutyl]acetamide, 28 g; $[\alpha]_D^{25} -32.6°$ (c 0.52, methanol).

Anal. Calcd for $C_8H_{16}ClNO_2$: C, 49.61; H, 8.33; N, 7.23. Found: C, 49.77; H, 8.07; N, 7.03.

EXAMPLE 31

(S)-5-(2-Methylpropyl)-3-morpholinone (S)-2-Chloro-N-[1-(hydroxymethyl)-3-methylbutyl]acetamide, 26.34 g (0.136 mol), is dissolved in 450 ml of tetrahydrofuran, the solution is cooled to 0°–5° C. and 7.8 g (0.195 mol) of 60% sodium hydride in mineral oil dispersion is slowly added. The mixture is allowed to reach room temperature and is stirred for 14 hours. Water, 10 ml, is added, the solvents evaporated in vacuo and the residue suspended in 250 ml of chloroform and washed with 100 ml of water and then a saturated aqueous solution of sodium chloride, 2×200 ml. The chloroform layer is separated, dried over sodium sulfate, and evaporated in vacuo. The residue is purified by chromatography using silica gel and eluting with dichloromethane methanol (95:5) to give (S)-5-(2-methylpropyl)-3-morpholinone, 5.1 g, mp 69°–70°; $[\alpha]_D^{25} -13.7°$ (c 1.11, methanol).

Anal. calcd for $C_8H_{15}NO_2$: C, 61.12; H, 9.62; N, 8.91. Found: C, 61.37; H, 10.06; N, 8.77.

EXAMPLE 32

(S)-[[4-Methyl-2[[(phenylmethoxy)carbonyl]amino]pentyl]oxy]acetic acid (S)-5-(2-Methylpropyl)-3-morpholinone, 3 g (0.019 mol), is suspended in a solution of 50 ml of concentrated hydrochloric acid and 50 ml of water, refluxed for four hours, cooled to room temperature, and extracted with 200 ml of dichloromethane. The aqueous layer is separated, evaporated in vacuo, the residue dissolved in 200 ml of water and the pH adjusted with a 10% aqueous solution of sodium hydroxide to pH 10–10.5. The solution is cooled to 5° C. and 3.73 g (0.022 mol) of benzylchloroformate is added dropwise while the pH is maintained at pH 10 with a 10% aqueous solution of sodium hydroxide. The mixture is stirred one hour, extracted with 100 ml of diethylether, the aqueous layer is separated and the pH is adjusted to pH 3–4 by the addition of a 10% aqueous solution of hydrochloric acid. The mixture is extracted with dichloromethane, 3×200 ml. The dichloromethane layer is separated, washed with a saturated aqueous solution of sodium chloride, 3×200 ml, separated, dried over sodium sulfate, evaporated and the residue is purified by chromatography using silica gel and eluting with dichloromethane-methanol (95:5) to give (S)-[[4-methyl2[[(phenylmethoxy)carbonyl]amino]pentyl]oxy]acetic acid, 5 g; $[\alpha]_D^{25} -30.5$ (c 0.55, methanol).

Anal. Calcd for $C_{10}H_{23}NO_5$: C, 62.12; H, 7.49; N, 4.53. Found: C, 62.04; H, 7.28; N, 4.32.

EXAMPLE 33

(S)-Phenylmethyl [1-[(2-amino-2-oxoethoxy)methyl]-3-methylbutyl]carbamate

Methylchloroformate, 0.87 g (0.009 mol), is added dropwise with stirring to a solution of 2.52 g (0.008 mol) of (S)-[[4-methyl-2[[(phenylmethoxy)carbonyl]amino]pentyl]oxy]acetic acid and 0.93 g (0.009 mol) of triethylamine in 100 ml of dichloromethane at −5°–10° C. The mixture is stirred for 30 minutes at −5° C., allowed to reach 0° C. and saturated with ammonia for five minutes. The mixture is allowed to reach room temperature and stirred for one hour, the solvent is evaporated in vacuo, the residue dissolved in 200 ml of dichloromethane, washed with a saturated aqueous solution of sodium chloride, 2×200 ml, the dichloromethane layer separated, dried over sodium sulfate and evaporated in vacuo. The residue is purified by chromatography using silica gel and eluting with dichloromethane-methanol (95:5) to give (S)-phenylmethyl-[1-[(2-amino-2-oxoethoxy)methyl]-3-methytbutyl]carbamate, 1.8 g, mp 78°–79°; $[\alpha]_D^{25} -22.1°$ (c 1.15, methanol).

Anal. Calcd for $C_{16}H_{24}N_2O_4$: C, 62.32; H, 7.85; N, 9.09. Found: C, 62.66; H, 7.70; N, 8.74.

EXAMPLE 34

[S-(R*,R*)]-Phenylmethyl-2-[[[1-[(2-amino-2-oxoethoxy)methyl]-3-methylbutyl]amino]carbonyl]-1-pyrrolidinecarboxylate A stirred suspension of 1.58 g (0.0051 mol) of (S)-phenylmethyl-[1-[(2 amino-2-oxoethoxy)methyl]-3- methylbutyl]carbamate and 0.3 g of 20% palladium on carbon in a 100 ml of methanol is exposed to hydrogen gas for 15 minutes, the suspension is purged with nitrogen gas, filtered, and the solvent evaporated in vacuo at 30° C. The residue is dissolved in 100 ml of dichloromethane, the solution is cooled to 0° C. and 1.3 g (0.0051 mol) of carbobenzyloxyproline, 0.78 g (0.0051 mol) of 1-hyroxybenzotriazole and 1.1 g (0.0051 mol) of dicyclohexylcarbodiimide are added. The mixture is allowed to reach room temperature and stirred for 14 hours, filtered, the solvent evaporated in vacuo and the residue dissolved in 200 ml of dichloromethane and washed successively with a 5% aqueous solution of sodium carbonate, 2×200 ml, 10% aqueous solution of citric acid, 2×200 ml and a saturated aqueous solution of sodium chloride, 2×200 ml. The dichloromethane layer is separated, dried over sodium sulfate, evaporated in vacuo and the residue purified by chromatography using silica gel and eluting with dichloromethane-methanol (95:5) to give [S-(R*,R*)]-phenylmethyl 2[[[1-[(2-amino-2-oxoethoxy)methyl]-3-methylbutyl]amino]-carbonyl]-1-pyrrolidinecarboxylate, 1.1 g; mp 146°–148°; $[\alpha]_D^{25}$ −55.3° (c 1.31, methanol).

Anal. Calcd for $C_{21}H_{31}N_3O_5$: C, 62.20; H, 7.71; N, 10.36. Found: C, 62.39; H, 7.43; N, 10.21.

EXAMPLE 35

[S-(R*,R*)]-Phenylmethyl 2-[[[1-[[2-(1,1-dimethylethoxy)-2-oxoethoxy]methyl]-3-methylbutyl]amino]carbonyl]-1-pyrrolidinecarboxylate (S)-[[4-Methyl-2[[(phenylmethoxy)carbonyl]amino]pentyl]oxy]acetic acid, 1.75 g (0.0057 mol) is dissolved in 50 ml of dichloromethane and the solution is placed in a pressure vessel, cooled under nitrogen gas to 5° C., 0.5 ml of concentrated sulfuric acid is added, the mixture is recooled to 5° C. and 10 ml of isobutylene is added. After 65.5 hours, the mixture is poured with stirring over a mixture of 1.35 g (0.0098 ml) of potassium carbonate, 50 ml of water, 50 g of ice and 50 ml of dichloromethane at such a rate that the temperature does not exceed 15° C. The dichloromethane layer is separated, washed with a saturated aqueous solution of sodium chloride, 2×200 ml, separated, dried over sodium sulfate and evaporated in vacuo. The residue is purified by chromatography using silica gel and eluting with dichloromethane-methanol (98:2) to give the intermediate t-butyl ester. A stirred suspension of 0.92 g (0.0025 mol) of the intermediate t-butyl ester and 0.2 g of 20% palladium on carbon in a 100 ml of methanol is exposed to hydrogen gas for 15 minutes, the suspension is purged with nitrogen gas, filtered and the solvent evaporated in vacuum at 30° C. The residue is dissolved in 100 ml of dichloromethane, the solution is cooled to 0° C. and 0.63 g (0.0025 mol) of carbobenzyloxyproline, 0.4 g (0.0025 mol) of 1-hydroxybenzotriazole and 0.52 g of dicylohexylcarbodiimide are added. The mixture is allowed to reach room temperature and stirred for 14 hours, filtered, the solvent evaporated in vacuo and the residue dissolved in 200 ml of dichloromethane and washed successively with a 5% aqueous solution of sodium carbonate, 2×200 ml, 10% aqueous solution of citric acid, 2×200 ml and a saturated aqueous solution of sodium chloride, 2×200 ml. The dichloromethane layer is separated, dried over sodium sulfate, evaporated in vacuo and the residue purified by chromatography using silica gel and eluting with dichloromethane-methanol (98:2) to give [S-(R*,R*)]phenylmethyl 2-[[[1-[[2-(1,1-dimethylethoxy)-2-oxoethoxy]methyl]-3-methylbutyl]amino]carbonyl]-1-pyrrolidinecarboxylate, 0.9 g; $[\alpha]_D^{25}$ −62.8° (c 0.56, methanol).

Anal. Calcd for $C_{25}H_{38}N_2O_6$: C, 64.91; H, 8.28; N, 6.06. Found: C, 64.93; H, 8.16; N, 6.12.

EXAMPLE 36

[S,(R*,R*)]-Phenylmethyl 2-[[[1-[(carboxy)methoxy]-3-methylbutyl]amino]carbonyl]-pyrrolidinecarboxylate

[S-(R*,R*)]-Phenylmethyl 2-[[1-[[2-(1,1-dimethylethoxy)-2-oxoethoxy]methyl]-3-methylbuty]amino]carbonyl]-1-pyrrolidine-carboxylate, 0.6 g (0.0013 mol), is dissolved in 20 ml of trifluoroacetic acid at 0° C. The mixture is allowed to stand 15 minutes at 0° C. and then allowed to reach room temperature over 30 minutes and the solvent evaporated in vacuo at 25° C. The residue is dissolved in 100 ml of dichloromethane and washed with a saturated aqueous solution of sodium chloride, 2×100 ml. The dichloromethane layer is separated, dried over sodium sulfate, evaporated in vacuo and the residue purified by chromatography using silica gel and eluting with dichloromethanemethanol (95:5) to give [S,R*,R*)]-phenylmethyl 2-[[[1-[(carboxy)methoxy]-3-methylbutyl]amino]carbonyl]pyrrolidinecarbonylate, 0.4 g, mp 118°–120°; $[\alpha]_D^{25}$ −69.6° (c 0.52, methanol).

Anal. Calcd for $C_{21}H_{30}N_2O_6$: C, 62.05; H, 7.44; N, 6.89. Found: C, 62.17; H, 7.27; N, 6.75.

EXAMPLE 37

(±)-[3-Phenyl-2-[[(phenylmethoxy)carbonyl]amino]propoxy]acetic acid (±)-5-(Phenylmethyl)-3-morpholinone, (U.S. Pat. No. 3,265,688) 5 g 0.026 mol), is suspended in a solution of 50 ml of concentrated hydrochloric acid and 50 ml of water and refluxed for six hours, cooled to room temperature and extracted with 200 ml of dichloromethane. The aqueous layer is separated, evaporated in vacuo, the residue dissolved in 200 ml of water, and the pH adjusted with a 10% aqueous solution of sodium hydroxide to pH 10–10.5. The solution is cooled to 5° C. and 5.1 g (0.03 mol) of benzylchloroformate is added dropwise while the pH is maintained at pH 10 with a 10% aqueous solution of sodium hydroxide. The mixture is stirred one hour, extracted with 100 ml of diethylether, the aqueous layer is separated and the pH is adjusted to pH 3–4 by the addition of a 10% aqueous solution of hydrochloric acid. The mixture is extracted with dichloromethane, 3×200 ml. The dichloromethane layer is separated, washed with a saturated aqueous solution of sodium chloride, 3×200 ml, separated, dried over sodium sulfate, evaporated and the residue is purified by chromatography using silica gel and eluting with dichloromethane-methanol (95:5) to give (±)-[3-phenyl[-2-[[(phenylmethoxy]carbonyl]amino]propoxy]acetic acid, 4 g; mp 96°–100°.

Anal. Calcd for $C_{19}H_{21}NO_5$: C, 66.46; H, 6.17; N, 4.08. Found: C, 66.03; H, 6.19; N, 4.05.

EXAMPLE 38

(±)-Phenylmethyl-[1-[(2-amino-2-oxoethoxy)methyl]-2-phenylethyl]carbamate

Methylchloroformate, 0.89 g (0.0094 mol) is added dropwise with stirring to a solution of 2.75 g (0.008 mol) of (±)-[3-phenyl-2-[[(phenylmethoxy)carbonyl]amino]propoxy]acetic acid and 0.96 g (0.0095 mol) of triethylamine in 100 ml of dichloromethane at −5°–10° C. The mixture is stirred for 30 minutes at −5° C., allowed to reach 0° C. and saturated with ammonia for 5 minutes. The mixture is allowed to reach room temperature and stirred for one hour, the solvent is evaporated in vacuo, the residue dissolved in 200 ml of dichloromethane, washed with a saturated aqueous solution of sodium chloride, 2×200 ml, the dichloromethane layer separated, dried over sodium sulfate, and evaporated in vacuo. The residue is purified by chromatography using silica gel and eluting with dichloromethane-methanol (95:5) to give (±)-phenylmethyl-[1-[(2-amino-2-oxoethoxy)methyl]-2-phenylethyl]carbamate, 2.5 g; mp 135°-137°.

Anal. Calcd for $C_{19}H_{22}N_2O_4$: C, 66.65; H, 6.48; N, 8.18. Found: C, 66.33; H, 6.60; N, 7.95.

EXAMPLE 39

(2S)-Phenylmethyl 2[[[1-[(2-amino-2-oxoethoxy)methyl]-2-phenylethyl]amino]carbonyl]-1-pyrrolidinecarboxylate (center on chain in 2 position is a mixture of isomers)

A stirred suspension of 1.52 g (0.0044 mol) of (±)-phenylmethyl [1-[(2-amino-2-oxoethoxy)methyl]-2-phenylethyl]-carbamate and 0.35 g of 20% palladium on carbon in a 100 ml of methanol is exposed to hydrogen gas for 15 minutes, the suspension is purged with nitrogen gas, filtered, and the solvent evaporated in vacuo at 30° C. The residue is dissolved in 100 ml of dichloromethane, the solution is cooled to 0° C. and 1.196 g (0.0048 mol) of carbobenzyloxyproline, 0.734 g (0.0048 mol) of 1-hydroxybenzotriazole and 0.99 g (0.0048 mol) of dicyclohexylcarbodiimide are added. The mixture is allowed to reach room temperature and stirred for 14 hours, filtered, the solvent evaporated in vacuo, and the residue dissolved in 200 ml of dichloromethane and washed successively with a 5% aqueous solution of sodium carbonate, 2×200 ml, 10% aqueous solution of citric acid, 2×200 ml and a saturated aqueous solution of sodium chloride, 2×200 ml. The dichloromethane layer is separated, dried over sodium sulfate, evaporated in vacuo and the residue purified by chromatography using silica gel and eluting with dichloromethane-methanol (95:5) to give (2S)-phenylmethyl 2-[[[1-[(2-amino-2-oxoethoxy)methyl]-2-phenylethyl]amino]carbonyl]-1-pyrrolidinecarboxylate (center on chain in 2 position is a mixture of isomers), 0.8 g; mp 137°-142°; $[\alpha]_D^{25}$ −45.1° (c 1.09, methanol).

Anal. Calcd for $C_{24}H_{29}N_3O_5$: C, 65.58; 1 H, 6.65; N, 9.56. Found: C, 65.70; H, 6.45; N, 9.70.

EXAMPLE 40

(2S)-Phenylmethyl 2-[[[1-[[2-(1,1-dimethylethoxy)-2-oxoethoxy]methyl]-2-phenylethyl]amino]carbonyl]-1-pyrrolidinecarboxylate (side chain in 2 position is (±) mixture)

(±)-(2-Amino-3-phenylpropoxy) acetic acid, monohydrochloride, 2.11 g (0.00838 mol) is suspended in 40 ml of hot p-dioxane and the solution is placed in a pressure vessel, 2.5 ml of concentrated sulfuric acid is added, the mixture is cooled to 5° C. and 20 ml of isobutylene is added. After 40 hours the mixture is poured with stirring over a mixture of 3.52 g (0.0534 mol) of 85% aqueous potassium hydroxide solution, 50 ml of water, 50 g of ice and 50 ml of dichloromethane at such a rate that the temperature does not exceed 15° C. The dichloromethane layer is separated, washed with a saturated aqueous solution of sodium chloride, 2×200 ml, separated, dried over sodium sulfate and evaporated in vacuo. The residue is purified by chromatography using silica gel and eluting with dichloromethane-methane (98:2) to give the intermediate t-butyl ester. The intermediate t-butyl ester, 1.6 g (0.006 mol), is dissolved in 100 ml of dichloromethane, the solution is cooled to 0° C. and 1.5 g (0.006 mol) of carbobenzyloxyproline, 0.92 g (0.006 mol) of 1-hydroxybenzotriazole and 1.24 g (0.006 mol) of dicyclohexylcarbodiimide are added. The mixture is allowed to reach room temperature and stirred for 14 hours, filtered, the solvent evaporated in vacuo, and the residue dissolved in 200 ml of dichloromethane and washed successively with a 5% aqueous solution of sodium carbonate, 2×200 ml, 10% aqueous solution of citric acid, 2×200 ml and a saturated aqueous solution of sodium chloride, 2×200 ml. The dichloromethane layer is separated, dried over sodium sulfate, evaporated in vacuo, and the residue purified by chromatography using silica gel and eluting with dichloromethane-methanol (99:1) to give (2S)-phenylmethyl 2-[[[1-[[2-(1,1-dimethylethoxy)-2-oxoethoxy]methyl]-2-phenylethyl]amino]carbonyl]-1-pyrrolidinecarboxylate (side chain in 2 position is (±) mixture), 1.5 g; $[\alpha]_D^{25}$ −59.4° (c 0.63, methanol).

Anal. Calcd for $C_{28}H_{36}N_2O_6$: C, 67.72; H, 7.31; N, 5.64. Found: C, 67.60; H, 7.31; N, 5.61.

EXAMPLE 41

(2S)-Phenylmethyl 2-[[[1-[(carboxymethoxy)methyl]-2-phenylethyl]amino]carbonyl]-1-pyrrolidinecarboxylate (center on chain in 2 position is a mixture of isomers)

(2S)-Phenylmethyl 2-[[[1-[[2-(1,1-dimethylethoxy)-2-oxoethoxy]methyl]-2-phenylethyl]amino]carbonyl]-1-pyrrolidinecarboxylate (side chain in 2 position is (±) mixture), 0.5 g (0.0010 mol), is dissolved in 30 ml of trifluoroacetic acid at 0° C. The mixture is allowed to stand 30 minutes at 0° C. and then allowed to reach room temperature over one hour and the solvent evaporated in vacuo at 25° C. The residue is dissolved in 100 ml of dichloromethane and washed with a saturated aqueous solution of sodium chloride, 2×100 ml. The dichloromethane layer is separated, dried over sodium sulfate, evaporated in vacuo, and the residue purified by chromatography using silica gel and eluting with dichloromethane methanol (95:5) to give (2S)-phenylmethyl 2-[[[1-[(carboxymethoxy)methyl]-2-phenylethyl]amino]carbonyl]-1-pyrrolidinecarboxylate (center on chain in 2 position is a mixture of isomers), 0.39 g; $[\alpha]_D^{25}$ −52.2° (c 0.23, methanol).

Anal. Calcd for $C_{24}H_{28}N_2O_6 1/4CH_3OH$: C, 64.94; H, 6.52; N, 6.25. Found: C, 64.67; H, 6.12; N, 6.33.

EXAMPLE 42

(2S)-1-(2-Bromo-4-methyl-1-oxopentyl)-2-pyrrolidinemethanol (2 position on side chain is RS mixture)

A solution of (±)-2-bromo-4-methyl-pentanoyl chloride, 21 g (0.099 mol), in 25 ml of acetone is added dropwise with stirring to a solution of 10 g (0.099 mol) of L-prolinol and 16.2 g (0.197 mol) of sodium acetate in a mixture of 150 ml of acetone and 75 ml of water at 0°-5° C. The mixture is stirred and allowed to reach room temperature over two hours, the solvent is evaporated in vacuo and the residue is suspended in 300 ml of chloroform and washed with water, 2×300 ml. The chloroform layer is separated, dried over sodium sulfate, evaporated in vacuo, and the residue is purified by chromatography using silica gel and eluting with dichloromethane-methanol (95:5) to give (2S)-1-(2-bromo-4-methyl-1-oxopentyl)2-pyrrolidinemethanol (2 position on side chain is R,S mixture), 21 g; mp 79°–82°; $[\alpha]_D^{25}$ −54.0° (c 0.6, methanol).

Anal. Calcd for $C_{11}H_{20}BrNO_2$: C, 47.49; H, 7.25; N, 5.04. Found: C, 47.44; H, 7.15; N, 4.86.

EXAMPLE 43

(8aS)-Tetrahydro-3-(2-methylpropyl)-1H-pyrrolo[2,1-c][1,4]oxazine-4(3H-one (2S)-1-(2-Bromo-4-methyl-1-oxopentyl)-2-pyrrolidinemethanol (2 position on side chain is R,S mixture), 19.48 g (0.07 mol), is dissolved in 500 ml of tetrahydrofuran, the solution is cooled to 0°–5° C. and 4 g (0.10 mol) of 60% sodium hydride in mineral oil dispersion is slowly added. The mixture is allowed to reach room temperature and is stirred for 14 hours and is then refluxed 2 hours. Water, 10 ml, is added, the solvents evaporated in vacuo and the residue suspended in 250 ml of chloroform and washed with 100 ml of water and the a saturated aqueous solution of sodium chloride, 2×200 ml. The chloroform layer is separated, dried over sodium sulfate, and evaporated in vacuo. The residue is purified by chromatography using silica gel and eluting with dichloromethane-methanol (97:3) to give (8aS)-tetrahydro-3-(methylpropyl)-1H-pyrrolo[2,1-c][1,4]oxazin-4(3H))-one, 8.3 g; mp 61°–65°; $[\alpha]_D^{25}$ −73.3° (c 0.57, methanol).

Anal. Calcd for $C_{11}H_{19}NO_2$: C, 66.97; H, 9.71; N, 7.10. Found: C, 67.22; H, 9.45; N, 6.92.

EXAMPLE 44

(2S)-Phenylmethyl 2-[(1-carboxy-3-methylbutoxy)methyl]-1-pyrrolidinecarboxylate (center on side chain is RS mixture)

(8a S-Tetrahydro-3-(2-methylpropyl-1H-pyrrolo[2,1-c][1,4] oxazine-4)3H)-one, 5.1 g (0.026 mol), is suspended in a solution of 50 ml of concentrated hydrochloric acid and 50 ml of water and refluxed for four hours, cooled to room temperature and extracted with 200 ml of dichloromethane. The aqueous layer is separated, evaporated in vacuo, the residue dissolved in 200 ml of water, and the pH adjusted with a 10% aqueous solution of sodium hydroxide to pH 10–10.5. The solution is cooled to 5° C. and 4.44 g (0.026 mol) of benzylchloroformate is added dropwise while the pH is maintained at pH 10 with a 10% aqueous solution of sodium hydroxide. The mixture is stirred one hour, extracted with 100 ml of diethylether, the aqueous layer is separated and the pH is adjusted to pH 3–4 by the addition of a 10% aqueous solution of hydrochloric acid. The mixture is extracted with dichloromethane, 3×200 ml. The dichloromethane layer is separated, washed with a saturated aqueous solution of sodium chloride, 3×200 ml, separated, dried over sodium sulfate, evaporated, and the residue is purified by chromatography using silica gel and eluting with dichloromethane-methanol (95:5) to give (2S)-phenylmethyl 2-[(1-carboxy-3-methylbutoxy)methyl]-1-pyrrolidinecarboxylate (center on side chain is R, S mixture), 4.3 g; $[\alpha]_D^{25}$ −78.7° (c 0.33, methanol).

Anal. Calcd for $C_{19}H_{27}NO_5$: C, 65.31; H, 7.79; N, 4.01. Found: C, 65.48; H, 7.72; N, 3.84.

EXAMPLE 45

(S)-Phenylmethyl 2-[[1-[[[2-(1,1-dimethylethoxy)-2-oxoethyl]amino]carbonyl]-3-methylbutoxy]methyl]-1-pyrrolidinecarboxylate (2-position of pentane chain is RS)

(2S)-Phenylmethyl-2-[(1-carboxy-3-methylbutoxy)-methyl]-1-pyrrolidinecarboxylate (center on side chain is R,S mixture), 2 g (0.0057 mol), is dissolved in 100 ml of dichloromethane, cooled to 0° C. and 1.1 g (0.0084 mol) of t-butylglycinate, 0.88 g (0.0057 mol) of 1-hydroxybenzotriazole and 1.32 g (0.0064 mol) of dicyclohexylcarbodiimide are added. The mixture is allowed to reach room temperature and stirred 14 hours, filtered, the solvent evaporated in vacuo and the residue dissolved in 200 ml of dichloromethane and washed successively with a 5% aqueous solution of sodium chloride, 2×200 ml. The dichloromethane layer is separated, dried over sodium sulfate, evaporated in vacuo and the residue purified by chromatography using silica gel and eluting with dichloromethane-methanol (98:2) to give (S)-phenylmethyl 2-[[1-[[[2-(1,1-dimethylethoxy)-2-oxoethyl]amino]carbonyl]-3-methoxy-butoxy]methyl]-1-pyrrolidinecarboxylate (2-position of pentane chain is R S), 1.75 g; $[\alpha]_D^{25}$ −70.2° (c 0.39, methanol).

Anal. Calcd for $C_{25}H_{38}N_2O_6$: C, 64.91; H, 8.28; N, 6.06. Found: C, 64.87; H, 8.46; N, 5.87.

EXAMPLE 46

(S)-Phenylmethyl 2-[[1-[[(carboxymethyl)amino]carbonyl]-3-methylbutoxy]methyl]-1-pyrrolidinecarboxylate (2-position of pentane chain is RS]

(S)-Phenylmethyl 2-[[1-[[[2-(1,1-dimethylethoxy)-2-oxoethyl]amino]carbonyl]-3-methylbutoxy]methyl]1-pyrrolidinecarboxylate (2-position of pentane chain is RS), 1.2 g (0.00259 mol), is dissolved in 30 ml of trifluoroacetic acid at 0° C. The mixture is allowed to stand 30 minutes at 0° C., and then allowed to reach room temperature over one hour and the solvent evaporated in vacuo at 25° C. The residue is dissolved in 100 ml of dichloromethane and washed with a saturated aqueous solution of sodium chloride, 2×100 ml. The dichloromethane layer is separated, dried over sodium sulfate, evaporated in vacuo and the residue purified by chromatography using silica gel and eluting with dichloromethane-methanol (95:5) to give (S)-phenylmethyl 2-[[1-[[(carboxymethyl)amino]carbonyl]-3-methylbutoxymethyl]-1-pyrrolidinecarboxylate (2-position of pentane chain is RS), 0.75 g; $[\alpha]_D^{25}$ −79° (c 0.34, methanol).

Anal. Calcd for $C_{21}H_{30}N_2O_6$: C, 62.05, H, 7.44; N, 6.89. Found: C, 62.38; H, 7.36; N, 6.69.

EXAMPLE 47

(2S)-Phenylmethyl 2-[[1-[[(2-ethoxy-2-oxoethyl)amino]carbonyl]-3-methylbutoxy]methyl]-1-pyrrolidinecarboxylate (center on side chain is RS mixture)

Triethylamine, 1.15 g (0.0114 mol), is added to 1.59 g (0.0114 mol of ethyl glycinate hydrochloride in 200 ml of dichloromethane at 0°. To the previous suspension at 0° C. is added 4 g (0.0114 mol) of (2S)-phenylmethyl 2-[(1-carboxy-3-methylbutoxy)methyl]-1-pyrrolidinecarboxylate (center on side chain is R,S mixture), 1.74 g (0.0114 mol) of 1-hydroxybenzotriazole and 2.35 g (0.0114 mol) of dicyclohexylcarbodiimide. The mixture is allowed to reach room temperature and stirred 14 hours, filtered, the solvent evaporated in vacuo and the residue dissolved in 200 ml of dichloromethane and washed successively with a 5% aqueous solution of sodium carbonate, 2×200 ml, 10% aqueous solution of citric acid, 2×200 ml, and a saturated aqueous solution of sodium chloride, 2×200 ml. The dichloromethane layer is separated, dried over sodium sulfate, evaporated in vacuo, and the residue purified by chromatography using silica gel and eluting with dichloromethanemethanol (98:2) to give (2S)-phenylmethyl 2-[[1-[[(2-ethoxy-2-oxoethyl)amino]carbonyl]-3-methylbutoxy]methyl]-1-pyrrolidinecarboxylate (center on side chain is R,S mixture), 4 g; $[\alpha]_D^{25} -72.7°$ (c 0.33, methanol).

Anal. Calcd for $C_{23}H_{34}N_2O_6$: C, 63.57; H, 7.89; N, 6.45. Found: C, 63.59; H, 7.84; N, 6.29.

EXAMPLE 48

(2S)-Phenylmethyl 2-[[1-[[(2-amino-2-oxoethyl)amino]carbonyl]-3-methylbutoxy]methyl]-1-pyrrolidinecarboxylate (center on side chain is RS mixture)

(2S)-Phenylmethyl-2-[[1-[[(2-ethoxy-2-oxoethyl)amino]carbonyl]-3-methylbutoxy]methyl]-1-pyrrolidinecarboxylate (center on side chain is R,S mixture), 2 g (0.0046 mol), is dissolved in 200 ml of methanol and the solution saturated with ammonia at room temperature. The solution is allowed to stand at room temperature for 14 hours and the solvent is evaporated in vacuo. The residue is purified by chromatography using silica gel and eluting with dichloromethanemethanol (90:10) to give (2S)-phenylmethyl 2-[[1-[[(2-amino-2-oxoethyl)amino]carbonyl]-3-methyl]butoxy]-methyl-1-pyrrolidinecarboxylate (center on side chain is R,S mixture), 1.6 g; $[\alpha]_D^{25} -76.9°$ (c 0.46, methanol).

Anal. Calcd for $C_{21}H_{31}N_3O_5$: C, 62.20; H, 7.71; N, 10.36. Found: C, 62.48; H, 7.35; N, 10.37.

EXAMPLE 49

(S)-1-(Chloroacetyl)-2-pyrrolidinemethanol

A solution of chloroacetyl chloride, 27.7 g (0.247 mol), in 66.5 ml of acetone is added dropwise with stirring to a solution of 25 g (0.247 mol) of L-prolinol and 40.4 g (0.493 mol) of sodium acetate in a mixture of 400 ml of acetone and 200 ml of water at 0°–5° C. The mixture is stirred and allowed to reach room temperature over two hours, the solvent is evaporated in vacuo and the residue is suspended in 300 ml chloroform and washed with water, 2×300 ml. The chloroform layer is separated, dried over sodium sulfate, evaporated in vacuo and the residue is purified by chromatography using silica gel and eluting with dichloromethanemethanol (98:2) to give (S)-1-(chloroacetyl)-2-pyrrolidinemethanol, 34.1 g; $[\alpha]_D^{25} -62.2°$ (c 1.00, methanol).

Anal. Calc for $C_7H_{12}ClNO_2$: C, 47.33; H, 6.81; N, 7.89. Found: C, 47.33; H, 6.60; N, 7.61.

EXAMPLE 50

Tetrahydro-1H-pyrrol[2,1-c][1,4]oxazin-4-(3H̄)-one (S)-1-(Chloroacetyl)-2-pyrrolidinemethanol, 12 g (0.068 mol), is dissolved in 500 ml of tetrahydrofuran, the solution is cooled to 0°–5° C., and 3.96 g (0.099 mol) of 60% sodium hydride in mineral oil dispersion is slowly added. The mixture is allowed to reach room temperature and is stirred for 14 hours. Water, 20 ml, is added, the solvents evaporated in vacuo, and the residue suspended in 300 ml of chloroform and washed with 100 ml of water and then a saturated aqueous solution of sodium chloride, 2×200 ml. The chloroform layer is separated, dried over sodium sulfate, and evaporated in vacuo. The residue is purified by chromatography using silica gel and eluting with dichloromethane-methanol (95:5) to give tetrahydro-1H-pyrrolo[2,1-c][1,4]oxazin-4-(3H̄)-one, 4.4 g; mp 63.5°–66°.

Anal. Calcd for $C_7H_{11}NO_2$: C, 59.55; H, 7.85; N, 9.92. Found: C, 59.41; H, 7.84; N, 9.83.

EXAMPLE 51

(S)-Phenylmethyl 2-[(carboxymethoxy)methyl]-1-pyrrolidinecarboxylate

Tetrahydro-1H-pyrrolo[2,1-c][1,4]oxazin-4-(3H̄)-one, 5 g (0.0354 mol), is suspended in a solution of 20 ml of concentrated hydrochloric acid and 20 ml of water and refluxed for four hours, cooled to room temperature and extracted with 200 ml of dichloromethane. The aqueous layer is separated, evaporated in vacuo, the residue dissolved in 200 ml of water, and the pH adjusted with a 10% aqueous solution of sodium hydroxide to pH 10–10.5. The solution is cooled to 5° C. and 7.25 g (0.0425 mol) of benzylchloroformate is added dropwise while the pH is maintained at pH 10 with a 10% aqueous solution of sodium hydroxide. The mixture is stirred one hour, extracted with 100 ml of diethylether, the aqueous layer is separated, and the pH is adjusted to pH 3–4 by the addition of a 10% aqueous solution of hydrochloric acid. The mixture is extracted with dichloromethane 3×200 ml. The dichloromethane layer is separated, washed with a saturated aqueous solution of sodium chloride, 3×200 ml, separated, dried over sodium sulfate, evaporated and the residue is purified by chromatography using silica gel and eluting with dichloromethane-methanol (95:5) to give (S)-phenylmethyl 2-[(carboxymethoxy)methyl]-1-pyrrolidinecarboxylate, 8 g; $[\alpha]_D^{25} -52.7°$ (c 1.1, methanol).

Anal. Calcd for $C_{15}H_{19}NO_5$: C, 61.42; H, 6.53; N, 4.78. Found: C, 61.21; H, 6.36; N, 4.60.

EXAMPLE 52

(S)-Phenylmethyl 2-[[[[[(ethoxycarbonyl)methyl]amino]carbonyl]methoxy]methyl]-1-pyrrolidinecarboxylate Triethylamine, 2.5 g (0.0247 mol), is added to 3.46 g (0.0248 mol) of ethyl glycinate hydrochloride in 200 ml of dichloromethane at 0° C. To the previous suspension at 0° C. is added 7.28 g (0.0248 mol of (S) phenylmethyl-2-[(carboxymethoxy)methyl]-1-pyrrolidinecarboxylate, 3.8 g (0.0247 mol) of 1-hydroxybenzotriazole and 5.1 g (0.0247 mol) of diicyclohexylcarbodiimide. The mixture is allowed to reach room temperature and stirred 14 hours, filtered, the solvent evaporated in vacuo and the residue dissolved in 200 ml of dichloromethane and washed successively with a 5% aqueous solution of sodium carbonate, 2×200 ml, 10% aqueous solution of citric acid, 2×200 ml and a saturated aqueous solution of sodium chloride, 2×200 ml. The dichloromethane layer is separated, dried over sodium sulfate, evaporated in vacuo, and the residue purified by chromatography using silica gel and eluting with dichloromethane-methanol (98:2) to give (S)-phenylmethyl 2-[[[[[(ethoxycarbonyl)methyl]amino]carbonyl]methoxy]- methyl]-1-pyrrolidinecarboxylate, 8.54 g; $[\alpha]_D^{25}$ −37.3° (c 0.82, methanol).

Anal. Calcd for $C_{19}H_{26}N_2O_6$: C, 60.30; H, 6.93; N, 7.40. Found: C, 60.46; H, 6.76; N, 7.33.

EXAMPLE 53

(S)-Phenylmethyl 2-[[[[(2-amino-2-oxoethyl)amino]carbonyl]methoxy]methyl]-1-pyrrolidinecarboxylate (S)-Phenylmethyl 2-[[[[[(ethoxycarbonyl)methyl]amino]carbonyl]methoxy]methyl]-1-pyrrolidinecarboxylate, 4 g (0.01057 mol), is dissolved in 100 ml of ethanol and the solution saturated with ammonia at room temperature. The solution is allowed to stand at room temperature for five days, the solvent evaporated in vacuo and the residue dissolved in 100 ml of methanol and the solution saturated with ammonia at room temperature. The solution is allowed to stand at room temperature for 14 hours and the solvent evaporated in vacuo. The residue is purified by chromatography using silica gel and eluting with dichloromethane-methanol (90:10) to give (S)-phenylmethyl 2-[[[[(2-amino-2-oxoethyl)amino]carbonyl]methoxy]methyl]-1-pyrrolidinecarboxylate, 3 g; mp 109.5°-111°; $[\alpha]_D^{25}$ −41.0° (c 0.57, methanol).

Anal. Calcd for $C_{17}H_{23}N_3O_5$: C, 58.44; H, 6.64; N, 12.03. Found: C, 58.40; H, 6.55; N, 11.77.

EXAMPLE 54

(S)-Phenylmethyl-2-[[[[[(carboxymethyl]amino]carboxy]methoxy]methyl]-1-pyrrolidinecarboxylate To a solution of 3.87 g (0.0102 mol) of (S)-phenylmethyl 2-[[[[(2-amino-2-oxoethyl)amino]carbonyl]methoxy]methyl]-1-pyrrolidinecarboxylate in 100 ml of methanol is added 0.816 g (0.0102 mol) of a 50% aqueous solution of sodium hydroxide. The mixture is allowed to stand at room temperature for four hours and the solvent evaporated in vacuo. The residue is dissolved in 200 ml of water, extracted with 200 ml of dichloromethane, the aqueous layer separated and the pH is adjusted to pH 3-4 by the addition of a 10% aqueous solution of hydrochloric acid. The mixture is extracted with dichloromethane, 3×200 ml. The dichloromethane layer is separated, washed with a saturated aqueous solution of sodium chloride, 3×200 ml, separated, dried over sodium sulfate, evaporated and the residue is purified by chromatography using silica gel and eluting with dichloromethane-methanol (95:5) to give (S)-phenylmethyl-2-[[[[(carboxymethyl)amino]carboxy]methoxy]methyl]-1-pyrrolidinecarboxylate, 1.75 g; $[\alpha]_D^{25}$ −41.7° (c 0.58, methanol).

Anal. Calcd for $C_{17}H_{22}N_2O_6$: C, 58.27; H, 6.33; N, 8.00. Found: C, 58.36; H, 6.30; N, 7.86.

EXAMPLE 55

[S]-N-[N-[[1-[(4-Methylphenyl)sulfonyl]-2-pyrrolidinyl]methyl]-L-leucyl]glycine, hydrochloride A solution of 3.00 g of (S)-N-[N-[[1-[(4-methylphenyl)sulfonyl]-2-pyrrolidinyl]methyl]-L-leucyl]glycine 1,1-dimethylethyl ester in 30 ml of trifluoroacetic acid is stirred at room temperature for 3.25 hours. The solvent is then removed under reduced pressure. The residue is dissolved in dichloromethane and the solvent removed under reduced pressure. This procedure is repeated several times. The residue is then dissolved in dichloromethane and anhydrous hydrogen chloride gas is passed through the solution. The solvent is removed under reduced pressure. The residue is dissolved in 25 ml of dichloromethane and added dropwise to 250 ml of ethyl ether. The solid is collected, washed with ethyl ether and dried in vacuo at 40° C. giving 2.18 g of a white solid, mp 148° (dec), $[\alpha]_D^{23}$ −61.0° (c 1, methanol).

EXAMPLE 56

(S)-1,1-Dimethylethyl N-[N-[[1-[(4-methylphenyl)sulfonyl]-2-pyrrolidinyl]methyl]-L-leucyl]glycinate To a solution of 3.00 g of carbobenzoxy-L-leucylglycine t-butyl ester in 30 ml of absolute ethanol is added 0.1 g of 20% palladium on charcoal. Hydrogen gas is passed through the mixture for 1.5 hours. The mixture is then filtered through Celite. To the filtrate is added 5 g of freshly activated 3 Å molecular sieves and 2.01 g of 2-pyrrolidinecarboxaldehyde, 1-[(4-methylphenyl)sulfonyl]. The mixture is stirred at room temperature for 1.5 hours. To the mixture is added a small amount of bromcresol green and 0.50 g of sodium cyanoborohydride. The color of the mixture is adjusted to yellow-green with a solution of hydrogen chloride gas in absolute ethanol. The mixture is stirred at room temperature for 72 hours then filtered. Solid citric acid is added to the filtrate until no further gas evolution is observed. The solvent is removed under reduced pressure. The residue is taken up in ethyl acetate, washed twice with water, then a saturated sodium bicarbonate solution until basic, and lastly a saturated brine solution. After drying over magnesium sulfate, the solvent is removed under reduced pressure giving 3.10 g of an oil which is used without further purification.

EXAMPLE 57

1-[(4-Methylphenyl)sulfonyl] 2-pyrrolidinecarboxaldehyde

To a mixture of 8.64 g of 1-[(4-methylphenyl)sulfonyl] 2-pyrrolidinemethanol and 14.2 ml of triethylamine in 100 ml of dry methyl sulfoxide is added slowly a solution of 16.16 g of sulfur trioxide pyridine complex in 100 ml of dry methyl sulfoxide. The solution is stirred at room temperature for one hour, then poured onto 1 l of ice water. The mixture is extracted with ethyl acetate. The combined organic extracts are washed with 1N citric acid (twice), water (twice), a saturated sodium bicarbonate solution then a saturated brine solution. After drying over magnesium sulfate, the solvent is removed under reduced pressure and the residue crystallized from chloroform/hexane. The solid is dried in vacuo at 40° giving 5.75 g of a solid, mp 136°-136.5° dec, $[\alpha]_D^{23}$ −121.0° (c 2, methanol).

EXAMPLE 58

1-[(4-Methylphenyl)sulfonyl], 2-pyrrolidinemethanol

Under nitrogen, 3.76 g of lithium borohydride is added to a cold solution of 12.23 g of N-[(4-methylphenyl)sulfonyl]proline methyl ester in 125 ml of dry tetrahydrofuran. The solution is stirred cold for one hour then at room temperature overnight. The solution is recooled and 69 ml of water is added carefully followed by 25 ml of concentrated hydrochloric acid/H₂O (1:1). The mixture is warmed slightly on a steam bath to separate the layers. The layers are separated and the aqueous layer is extracted with ethyl acetate. The combined organic extracts are washed with water, a saturated sodium bicarbonate solution, then a saturated brine solution. After drying over magnesium sulfate, the solvent is removed under reduced pressure and the residue crystallized from chloroform/hexane. The solid is dried in vacuo at 40° C. giving 8.69 g of a white solid, mp 82°–84°, $[\alpha]_D^{23} -83.4°$ (c 2, methanol).

EXAMPLE 59

N-[(4-Methylphenyl)sulfonyl]proline,methyl ester

To a cold solution of 20.0 g of proline methyl ester hydrochloride in 110 ml of purified pyridine is added 23.5 g of 4-methylphenylsulfonyl chloride. The mixture is stirred overnight allowing the ice bath to melt. The mixture is recooled and diluted with 550 ml of cold ethyl acetate. The mixture is washed with 280 ml of cold water, 280 ml of cold 6N hydrochloric acid, 250 ml of water, 250 ml of a saturated sodium bicarbonate solution then 250 ml of a saturated brine solution. After drying over magnesium sulfate, the solvent is removed under reduced pressure and the residue crystallized from chloroform/hexane. The solid is dried in vacuo at 45° C. giving 12.91 g of a white solid, mp 75°–77°, $[\alpha]_D^{23} -119.4°$ (c 2, methanol).

EXAMPLE 60

Carbobenzoxy-L-leucylglycine, 1,1-dimethylethyl ester

To a cold solution of 5.00 g of carbobenzoxy-L-leucine, 2.55 g of 1-hydroxybenzotriazole hydrate and 2.47 g of glycine 1,1-dimethylethyl ester in 100 ml of 1:1 acetonitrile/tetrahydrofuran is added dropwise a solution of 3.89 g of N,N-dicyclohexylcarbodiimide in 40 ml of tetrahydrofuran. The solution is stirred overnight allowing the ice bath to melt. The mixture is filtered and the solvent removed under reduced pressure. The residue is dissolved in ethyl acetate and washed with water, a 0.1M citric acid solution, a saturated sodium bicarbonate solution and then a saturated brine solution. After drying over magnesium sulfate, the solvent is removed under reduced pressure. The residue is chromatographed on silica gel eluting with 7:3 chloroform/ethyl acetate giving 6.68 g of an oil.

EXAMPLE 61

Synthesis of BOC-D-leucylglycinamide 1.55 g (0.014 mole) of glycinamide hydrochloride is dissolved in 50 ml of DMF by warming to 50°. The solution is cooled to 25° and 2 ml of triethylamine is added, followed by 1.89 g of hydroxybenztriazole, 3.5 g (0.014 mol) of BOC-D-leucine H₂O and lastly, 2.9 g (0.014 mol) of dicyclohexylcarbodiimide. The mixture is stirred two days at 25° and then evaporated in vacuo to an oil. The oil is dissolved in 200 ml EtOAC, 50 ml CHCl₃. The organic solution is washed with water, 20% citric acid solution, water, 10% Na₂CO₃ solution. The EtOAc solution is dried over MgSO₄ and the solvent removed in vacuo to a glass, 3.7 g (93%).

Anal. Calcd for $C_{13}H_{25}N_3O_4.1/4CHCl_3$: C, 49.22; H, 7.94, N, 13.25. Found: C, 48.57; H, 7.95; N, 12.52.

EXAMPLE 62

1-[(4-Methylphenyl)sulfonyl]-2-pyrrolidinemethanol

To a stirred solution of 17 g (0.168 mole) of L-pyrrolidine-2-methanol in 100 ml of H₂O at 10° is added 32 g (0.168 mol) of p-toluenesulfonyl chloride in 100 ml of acetone over a 30 minute period. The pH of the solution is maintained at 11 by the addition of 2N NaOH solution. After stirring one hour more, the solution is evaporated in vacuo to one-half volume and acidified with conc. HCl. The solution is extracted with EtOAc, the EtOAc dried over MgSO₄ and evaporated to an oil. The oil crystallized from ether-cyclohexane, 35 g (83%), mp 90°–91°; $[\alpha]_D^{23} -89.4°$ (c 1, methanol).

Anal. Calcd for $C_{12}H_{17}NO_3S$: C, 56.44; H, 6.71; N, 5.49. Found: C, 56.51; H, 6.51; N, 5.41.

1-[(4-Methylphenyl)sulfonyl]-2-pyrrolidinecarboxaldehyde

To a stirred solution of 5 g (0.0394 mol) of oxalyl chloride in 50 ml of CH₂Cl₂ at −60° is added dropwise 7 g (0.0833 mol) of DMSO. The solution is stirred 30 minutes at −60° and then 10 g (0.039 mol) of N-tosylprolinol is added over five minutes at 60° and 15 ml of triethylamine is added. The solution is warmed to 25° and stirred one hour. The solution is then washed with H₂O, dried over MgSO₄ and the solvents removed. The residual oil, 10 g, is purified using a silica gel column and CHCl₃:MeOH (90:10) as the eluates. An oil is obtained which solidifies, 9.5 g (96%), mp 139°–140°.

Anal. Calcd for $C_{12}H_{15}NO_3S$: C, 56.89; H, 5.97; N, 5.53. Found: C, 56.73; H, 6.11; N, 5.39.

EXAMPLE 63

Synthesis of (S)-N²-[[1-[(4-Methylphenyl)sulfonyl]-2-pyrrolidinyl]-methyl]-D-Leucylglycinamide To a solution of 3.5 g (0.012 mole) of BOC-D-leuylglycinamide in 20 ml of CH₂Cl₂ at 25° is added 20 ml of trifluoroacetic acid. The solution is left for 15 minutes at 25°. The solvents are evaporated in vacuo. Ether gives a gummy solid which is washed five times with ether and dried in vacuo. The solid is dissolved in 100 ml of methanol and triethylamine added until the solution is basic to test paper (pH 9). 3 g (0.012 mol) of tosylproline aldehyde is added, 50 ml of dried 3 Å sieves and 3 g (0.048 mol) of sodium cyanoborohydride. The pH of the mixture is brought to 5–6 with solid citric acid and the mixture is stirred for five days at 25° C. The mixture is filtered, the methanol evaporated, and the residue is taken up in EtOAc. The EtOAc solution is extracted with H₂O, the aqueous layer is made basic with Na₂CO₃ and extracted with EtOAc. The EtOAc solution is dried and evaporated to an oil, 3 g. The oil is put through a silica gel column using CHCl₃:MeOH (90:10) as solvent. The one spot eluted fractions are pooled and evaporated to a clear oil, 2.5 g (49%) IR bands; 1660, 1520, 1340, 1160, 665, 585, 550. NMR bands: 0.8, 0.9, 1.7, 3.0, 3.8 (quartet), 7.2, 7.3, 7.5, 7.6.

Anal. Calcd for $C_{20}H_{32}N_4O_4S.1/2H_2O$: C, 55.40; H, 7.68; N, 12.92. Found: C, 54.93; H, 7.28; N, 12.80.

EXAMPLE 64

[2S-[2R*(2R,4R*)]]-N-[4-Methyl-2-[[[1-[(4-methylphenyl)-sulfonyl]-2-pyrrolidinyl]methyl]amino]pentyl]glycine, dihydrochloride A solution of 4.98 g of [S-(R*,R*)]-N-[(1,1-dimethylethoxy)carbonyl]-N-[4-methyl-2-[[[1-[(4-methylphenyl)sulfonyl]-2-pyrrolidinyl]methyl]amino]pentyl]glycine, 1,1-dimethylethyl ester, in 40 ml of trifluoroacetic acid is stirred at room temperature for two hours. The solvent is then removed under reduced pressure. The residue is dissolved in dichloromethane and the solvent removed under reduced pressure. This procedure is repeated several times. The residue is then dissolved in dichloromethane and anhydrous hydrogen chloride gas is passed through the solution. The solvent is removed under reduced pressure. The residue is dissolved in 20 ml dichloromethane and added dropwise to 200 ml ethyl ether. The solid is collected, washed with ethyl ether, and dried in vacuo at 50° C. giving 3.53 g of a white solid, mp 138° (dec), $[\alpha]_D^{23} -69.1°$ (c 2, methanol).

EXAMPLE 65

[S-(R*,R*)]N-[(1,1-Dimethylethoxy)carbonyl]-N-[4-methyl-2-[[[1-[(4-methylphenyl)sulfonyl]-2-pyrrolidinyl]-methyl]amino]pentyl]glycine, 1,1-dimethylethyl ester To a solution of 6.00 g of (S)-N[(1,1-dimethylethoxy)carbonyl]-N-[4-methyl-2-[[(phenylmethoxy)carbonyl]amino]pentyl]glycine,1,1-dimethylethyl ester in 60 ml of absolute ethanol is added 0.3 g of 20% palladium on charcoal. Hydrogen gas is passed through the mixture for 2.25 hours. The mixture is filtered through Celite and 0.1 g of fresh catalyst is added. Hydrogen gas is passed through for 0.5 hours. The mixture is filtered through Celite. To the filtrate is added 6 g of freshly activated 3 Å molecular sieves and 3.27 g of 1-[(4-methylphenyl)sulfonyl]2-pyrrolidinecarboxaldehyde. The mixture is stirred at room temperature for 1.5 hours. To the mixture is added a small amount of bromcresol green and 0.81 g of sodium cyanoborohydride. The color of the mixture is adjusted to yellow-green with a solution of hydrogen chloride gas in absolute ethanol. The mixture is stirred at room temperature for 72 hours then filtered. Solid citric acid is added to the filtrate until no further gas evolution is observed. The solvent is removed under reduced pressure. The residue is taken up in ethyl acetate, washed twice with water, then a saturated sodium bicarbonate solution until basic and lastly a saturated brine solution. After drying over magnesium sulfate, the solvent is removed under reduced pressure. The residue is chromatographed on 350 g of silica gel eluting with 3:2 chloroform/ethyl acetate giving 5.03 g of an oil.

EXAMPLE 66

(S)-N-[(1,1-Dimethylethoxy)carbonyl]-N-[4-methyl-2-[[(phenylmethoxy)carbonyl]amino]pentyl]glycine, 1,1-dimethylethyl ester To a solution of 8.37 g of N-[4-methyl-2-[[(phenylmethoxy)carbonyl]amino]pentyl]glycine, 1,1-dimethylethyl ester in 85 ml of dichloromethane is added a solution of 5.51 g of di-t-butyl dicarbonate in 15 ml of dichloromethane. The solution is stirred at room temperature overnight. An additional 2.01 g of di-t-butyl dicarbonate is added and the solution is stirred for 3.5 hours. The solvent is removed under reduced pressure. The residue is chromatographed on 670 g silica gel eluting with 95:5 chloroform/ethyl acetate then 9:1 chloroform/ethyl acetate giving 9.95 g of an oil.

EXAMPLE 67

(S),N-[4-Methyl-2-[[(phenylmethoxy)carbonyl]amino]-pentyl]glycine, 1,1-dimethylethyl ester A solution of 10.00 g of (S)-1-aziridinecarboxylic acid, 2-(2-methylpropyl)phenylmethyl ester and 11.25 g of glycine t-butyl ester in 100 ml of absolute ethanol is refluxed for 48 hours. The solvent is removed under reduced pressure. The residue is chromatographed on 1 kg silica gel eluting with 7:3 chloroform/ethyl acetate giving 8.54 g of an oil.

EXAMPLE 68

[S-(R*,R*)]-N-[4-Methyl-2-[[[1-[(4-methylphenyl)sulfonyl]-2-pyrrolidinyl]carbonyl]amino]pentyl]glycine, monohydrochloride A solution of 4.72 g of [S-(R*,R*)]-N-[(1,1-dimethylethoxy)carbonyl]-N-[4-methyl-2-[[[1-[(4-methylphenyl)sulfonyl]-2-pyrrolidinyl]carbonyl]amino]pentyl]glycine-1,1-dimethylethyl ester in 50 ml of trifluoroacetic acid is stirred at room temperature for 2.5 hours. The solvent is then removed under reduced pressure. The residue is dissolved in dichloromethane and the solvent removed under reduced pressure. This procedure is repeated several times. The residue is then dissolved in dichloromethane and anhydrous hydrogen chloride gas is passed through the solution. The solvent is removed under reduce pressure giving a foam which is suspended in ethyl ether to solidify. The solid is collected, washed with ethyl ether and dried in vacuo at 45° C. giving 3.44 g of a white amorphous solid, mp 175° (dec), $[\alpha]_D^{23} -120.5°$ (c 2, methanol).

EXAMPLE 69

[S-(R*,R*)]-N-[(1,1-Dimethylethoxy)carbonyl]-N-[4-methyl-2-[[[1-[(4-methylphenyl)sulfonyl]-2-pyrrolidinyl]carbonyl]amino]pentyl]glycine, 1,1-dimethylethyl ester To a cold solution of 2.87 g of N-[(4-methylphenyl)sulfonyl]proline, 1.30 g of 1-hydroxybenzotriazole hydrate and 3.17 g of glycine, N-(2-amino-4-methylpentyl)-N-[(1,1-dimethylethoxy)carbonyl]-1,1-dimethylethyl ester (S) in 30 ml of N,N-dimethylformamide is added dropwise a solution of 1.98 g of N,N-dicyclohexylcarbodiimide in 10 ml of N,N-dimethylformamide. The solution is stirred overnight allowing the ice bath to melt. The mixture is filtered and the solvent removed under high vacuum. The residue is taken up in ethyl acetate and filtered. The filtrate is washed with water, a saturated sodium bicarbonate solution, a saturated brine solution, and then dried over magnesium sulfate. After removing the solvent under reduced pressure, the residue is chromatographed on 300 g of silica gel eluting with chloroform/ethyl acetate (7:3) giving 5.21 g of an oil, $[\alpha]_D^{23} -80.3°$ (c 2, methanol).

EXAMPLE 70

(S)-2-Formyl-1-pyrrolidine carboxylic acid, phenylmethyl ester

To a flame dried, N₂ purged 1 l flask is added 20 g L-carbobenzoxy proline and 250 ml tetrahydrofuran distilled from sodium aluminum hydride. Cool to 3° C. Charge 14.32 g carbonyldiimidazole and stir 30 minutes at 3° C. Cool the mixture to −45° C. and add 250 ml 1M diisobutyl aluminum hydride in hexane, over 10 minutes. Stir an additional 35 minutes upon completion of the addition.

Add 500 ml cold 1N hydrochloric acid with foaming and warming to −10° C. Warm the mixture to 25° C. and separate phases. The aqueous phase is twice extracted with 250 ml ethyl acetate and these extracts are combined with the organic phase of the previous separation. This combined organic phase is extracted once with 400 ml 6% hydrochloric acid, twice with 250 ml saturated sodium bicarbonate solution, and once with 250 ml saturated sodium chloride solution. The organic phase is dried over anhydrous magnesium sulfate, filtered, and stripped in vacuo to an oil, 17.5 g, 93% yield. NMR indicates the presence of an aldehydic proton at 9.4 ppm in deuterochloroform. The oil is sufficiently pure for use in the following steps.

EXAMPLE 71

[S-(R*,R*)]-2-[[[[1-[(2-Amino-2-oxoethyl)amino]carbonyl]-3-methylbutyl]amino]methyl]-1-pyrrolidinecarboxylic acid, phenylmethyl ester To a flame dried, $N_2$ purged flask, add 17.47 g (S)-2-formyl-1-pyrrolidine carboxylic acid, phenylmethyl ester, L-leucylglycineamide and 600 ml dry, distilled tetrahydrofuran. Add 120 g 5 Å molecular sieves (predried at 400° C. overnight) and stir at 25° C. overnight. Filter, strip in vacuo to an oil. Charge 500 ml dry, absolute ethanol to the oil, followed by a few crystals of bromocresol green. Cool to 3° C. and add 8.17 g sodium cyanoborohydride. Adjust the color of the mixture to green by the dropwise addition of a cold solution of anhydrous hydrogen chloride gas in ethanol. Stir two hours at 3° C. then warm to 25° C. overnight. Continue stirring for two days at 25° C. Add 119 g citric acid, with foaming and exotherm. Strip the solvent from the mixture under vacuum, giving a resin.

Partition the resin between 500 ml water and 500 ml ethyl acetate. Separate phases and dilute the aqueous phase with 400 ml water. Saturate with solid sodium bicarbonate and extract once with 500 ml ethyl acetate. Wash with ethyl acetate phase once with 250 ml saturated sodium chloride solution, dry over anhydrous magnesium sulfate, filter, and strip filtrate of solvent in vacuo to a white foam, 12.99 g. The foam is chromatographed on 300 g silica gel, eluted with 5/95 methanol/chloroform. Those fractions containing product are stripped of solvent in vacuo to an oil, and are crystallized from methylene chloride/ethyl ether, giving a white solid, 8.33 g, 32% yield, mp 98°–99°, $[\alpha]_D^{23}$ −62.6° (c 1.07, methanol). $R_f$ 0.34 on Merck SG60 TLC plates eluted with 10/90 methanol/chloroform.

EXAMPLE 72

[S-(R*,R*)]-2-[[[1-[(1,1-Dimethylethoxy)carbonyl]-3-methylbutyl]amino]methyl]1-Pyrrolidine carboxylic acid, phenylmethyl ester To a flame dried, $N_2$ purged flask was charged 600 ml dry tetrahydrofuran, 15.76 g (S)-2-formyl-1-pyrrolidinecarboxylic acid, phenylmethyl ester (prepared as previously described), 80 g 5 Å molecular sieves (predried at 400° C. overnight) and 12.65 g L-leucine t-butyl ester. Stir at 25° C. overnight, filter, and strip to a hazy oil, 31.45 g. To the oil add 330 ml dry absolute ethanol and a few crystals of bromocresol green. Cool to 5° C. Add 4.24 g sodium cyanoborohydride and adjust color of the mixture to green by the dropwise addition of a cold solution of anhydrous hydrogen chloride gas in ethanol. Stir one hour at 5° C. then warm to 25° C. and stir for three days. Add 70 g citric acid over one hour with offgassing, strip off ethanol under vacuum, and dissolve the resulting resin in 500 ml ethyl acetate. Wash once with 250 ml water, twice with 400 ml saturated sodium bicarbonate solution, and once with 50 ml saturated sodium chloride soluton. Dry the organic phase over magnesium sulfate (anhydrous), filter, and strip filtrate under vacuum to an oil, 24.1 g. Chromatograph on 1000 g silica gel, eluting with 50/50 hexane/ethyl acetate. Recover 14.0 g of an oil, 51% yield.

$[\alpha]_D^{23}$ −49.4° (c 1.06, methanol). $R_f$=0.54 on Merck SG60 TLC plates, eluted with 50/50 hexane/ethyl acetate.

EXAMPLE 73

[S-(R*,R*)]-2-[[(1-Carboxy-3-methylbutyl)amino]methyl]-1-pyrrolidinecarboxylic acid, phenylmethyl ester hydrochloride To a 100 ml flask containing 11.88 g of 1-pyrrolidinecarboxylic acid, 2-[[[1-[(1,1-dimethylethoxy)carbonyl]-3-methylbutyl]amino]methyl]-phenylmethyl ester, [S-(R*,R*)]-add 50 ml trifluoroacetic acid and stir at 25° C. for two hours. Dilute with 20 ml methylene chloride and strip to an oil. Repeat three times. Take up oil into ethyl ether and add a solution of ethyl ether saturated with anhydrous hydrogen chloride gas, giving a precipitate. Decant solvent and dry the solid in vacuo at 40° C., giving a hygroscopic solid, 8.52 g, 76% yield, $[\alpha]_D^{23}$ −13.5° (c 1.23, methanol).

EXAMPLE 74

[S-(R*,R*)]-2-[[[1-[(2-Amino-2-oxoethyl)amino]carbonyl]-3-methylbutyl]amino]methyl]1-pyrrolidonecarboxylic acid, phenylmethyl ester To a 250 ml flask containing 1.40 g (S)-N-[N-[1-[(phenylmethoxy)carbonyl]-2-pyrrolidinyl]-L-leucyl]glycine methyl ester add 50 ml methanol, cool to 3° C. and saturate with anhydrous ammonia gas over five minutes. Stopper the flask and stir overnight. Remove the solvent in vacuo at less than 40° C. giving a white foam, 1.4 g. Chromatograph on 50 g silica gel, eluting with 10/90 methanol/chloroform. Recover a clear resin, 1.39 g. Triturate with ethyl ether, giving a solid. Wash with petroleum ether and dry in vacuo at 40° C. giving a white solid, 1.18 g, mp 98°–99°. $[\alpha]_D^{23}$ −61.0° (c 1.06, methanol).

EXAMPLE 75

(S)-N-[N-[1-[(Phenylmethoxy)carbonyl]-2-pyrrolidinyl]-L-Leucyl]glycine, methyl ester To a 500 flask containing 7.33 g [S-(R*,R*)]-2-[[(1-carboxy-3-methyl butyl)amino]methyl]-1-pyrrolidinecarboxylic acid, phenylmethyl ester hydrochloride add 150 ml dimethylformamide and cool to −5° C. Add 2.57 g 1-hydroxybenzotriazole, 2.39 g glycine methyl ester hydrochloride, and 5.35 ml triethylamine. Add a solution of 3.98 g dicyclohexylcarbodiimide in 50 ml dimethylformamide over five minutes. Stir and allow to warm to 25° C. overnight. Filter and strip filtrate in vacuo to a paste. Take up into 100 ml ethyl acetate and filter. Wash filtrate once with 75 ml water, twice with 50 ml saturated sodium bicarbonate solution and once with 25 ml sodium chloride solution. Dry organic phase over anhydrous magnesium sulfate, filter and strip in vacuo to an oil. Chromatograph on 200 g silica gel, eluting with 5/95 methanol/chloroform, recovering an oil, 1.41 g, 18% yield. $R_f$ 0.52 on Merck SG60 TLC plates, eluted with 10/90 methanol/chloroform.

Mass Specrometry detects the molecular ion at 402.2. Additional fragmentation supports anticipated structure.

EXAMPLE 76

[S-(R*,R*)]-2-[[[1-[[[2-(1,1-Dimethylethoxy)-2-oxoethyl]thio]methyl]-3-methylbutyl]amino]methyl]-1-pyrrolidinecarboxylic acid, phenylmethyl ester To a 500 ml flask containing (S)-2-formyl-1-pyrrolidinecarboxylic acid, phenylmethyl ester add 250 ml dry, distilled tetrahydrofuran, and 70 g 5 Å molecular sieves (predried at 400° C.). Add 6.88 g (S)-[(2-amino-4-methylpentyl)thio]acetic acid, 1,1-Dimethylethyl ester and stir at 25° C. overnight.

Filter and strip filtrate in vacuo to a yellow oil, 14.6 g. Dissolve in 130 ml dry absolute ethanol and cool to 5° C. Add a few crystals of bromocresol green followed by 1.73 g sodium cyanoborohydride. Adjust color to green by the dropwise addition of a cold solution of anhydrous hydrogen chloride gas in ethanol. Stir one hour at 5° C. then at 25° C. for three days.

Add 31 g citric acid with foaming and stir one hour. Strip in vacuo to a syrup. Dissolve in 250 ml ethyl acetate, and wash once with 75 ml water, twice with 200 ml saturated sodium bicarbonate solution, and once with 50 ml saturated sodium chloride solution. The organic phase was dried over anhyrous magnesium sulfate, filtered, and stripped in vacuo to a bluish oil, 13.11 g. Chromatograph on 500 g silica gel, eluting with 10/90 methanol/chloroform, recovering a yellow oil, 10.3 g, 80% yield. $[\alpha]_D^{23} -21.4°$ (c 0.98, methanol). $R_f=0.63$ on Merck SG60 TLC plates eluted with 10/90 methanol/chloroform.

EXAMPLE 77

[S-(R*,R*)]-2-[[[1-[[(Carboxymethyl)thio]methyl]-3-methylbutyl]amino]methyl]-1-pyrrolidonecarboxylic acid, phenylmethyl ester To a 500 ml flask containing 8.29 g of [S-(R*,R*)]-2-[[[1-[[[2-(1,1-dimethylethoxy)-2-oxoethyl]thio]methyl]-3-methylbutyl]amino]methyl]-1-pyrrolidonecarboxylic acid, phenylmethyl ester charge 100 ml trifluoroacetic acid, stir 2.5 hours at 25° C. and strip in vacuo to an oil. Add 100 ml methylene chloride and strip to an oil. Add 100 ml methylene chloride, saturate with anhydrous hydrogen chloride gas, and strip to an oil. Repeat once. Dissolve in 50 ml ethyl acetate and adjust pH to 4 with saturated sodium bicarbonate solution. Wash the mixture twice with 25 ml saturated sodium chloride solution and dry the organic phase over anhydrous magnesium sulfate. Filter and strip in vacuo to an oil, 7.75 g. Chromatograph on 300 g silica gel, eluting with 10/90 methanol/chloroform, recovering a yellow resin, 3.81 g. Dissolve in methylene chloride and precipitate by addition to 250 ml petroleum ether, giving a gum. Cool to −50° C. and decant solvent. Dry residue in vacuo, 25° C., giving 3.48 g of a white foam, 44% yield. $[\alpha]_D^{23} -16.1°$ (c 1.1, methanol). $R_f=0.29$ on Merck SG60 TLC plates eluted with 10/90 methanol/chloroform.

EXAMPLE 78

[S-(R*,R*)]-2-[[[1-[[(Carboxymethyl)thio]methyl]-3-methylbutyl][(1,1-dimethylethoxy)carbonyl]amino]methyl]-1-pyrrolidinecarboxylic acid, phenylmethyl ester To a 1 l flask containing 12.84 g of [S-(R*,R*)]2-[[[1-[[(carboxymethyl)thio]methyl]-3-methylbutyl]amino]methyl]-1-pyrrolidinecarboxylic acid, phenylmethyl ester add 200 ml methylene chloride, 6.78 ml triethylamine, and 5.34 g ditertbutyl dicarbonate. Stir at 25° C. overnight. Add 1.0 g di-tert-butyl dicarbonate, stir at 25° C. for eight hours, then refrigerate for three days.

Strip in vacuo to a paste, dissolve in a minimum amount of ethyl acetate and filter. Chromatograph on 300 g silica gel, eluting with 10/90 methanol/chloroform. Recover a hazy oil, 3.87 g, 35% yield. $R_f=0.39$ Merck SG60 TLC plates eluted with 10/90 methanol/chloroform. The material is sufficiently pure to use in the next step.

EXAMPLE 79

[S-(R*,R*)]-2-[[[1-[[(2-Amino-2-oxoethyl)thio]methyl]-3-methylbutyl][(1,1-Dimethylethoxy)carbonyl]amino]methyl]-1-[pyrrolidine]carboxylic acid, phenylmethyl ester To a 250 ml flask, add 150 ml dry, distilled tetrahydrofuran and 3.87 g [S-(R*,R*)]-2[[[1-[[(carboxymethyl)thio]methyl]-3-methylbutyl][(1,1-dimethylethoxy)carbonyl]amino]methyl]-1-pyrrolidine carboxylic acid, phenylmethyl ester. Cool to 0° C. and add 0.84 ml N-methylmorpholine followed by 1.04 ml isobutylchloroformate. A solid forms. Stir 15 minutes, then sparge with anhydrous ammonia gas, giving a thick, white precipitate. Stir two hours at 5° C., followed by two hours at 25° C. Filter, and wash the solid with 50 ml tetrahydrofuran. Strip the filtrate in vacuo to an oil 4.26 g. Chromatograph the oil on 200 g silica gel, eluting with 15/85 hexane/ethyl acetate. Recover a foam, 2.68 g, 69% yield. $[\alpha]_D^{23} +16.6°$ (c=1.07, methanol). $R_f=0.50$ on Merck SG60 TLC plates, eluted with 10/90 methanol/chloroform.

EXAMPLE 80

[S-(R*,R*)]-2-[[[1-[[(2-Amino-2-oxoethyl)thio]methyl]-3-methylbutyl]amino]methyl]-1-pyrrolidinecarboxylic acid, phenylmethyl ester, monohydrochloride To a 100 ml flask containing 2.46 g [S-(R*,R*)]-2-[[[1-[[(2-amino-2-oxoethyl)thio]methyl-3-methylbutyl][(1,1-dimethylethoxy)carbonyl]amino]methyl]1-pyrrolidinecarboxylic acid, phenylmethyl ester, add 75 ml methylene chloride and saturate with anhydrous hydrogen chloride gas. Stir two hours and strip in vacuo to a foam. Dissolve in a minimum amount of methylene chloride and precipitate by addition to ethyl ether. Filter the solid and dry in vacuo at 40° C., giving a hygroscopic foam, 1.7 g, 79% yield. $[\alpha]_D^{23} -5.9°$ (c 1.28, methanol). $R_f=0.31$ on Merck SG60 TLC plates, eluted with 10/90 methanol/chloroform.

EXAMPLE 81

(S)-2-[[[1-[[[2-(1,1-Dimethylethoxy)-2-oxoethyl]amino]methyl]-3-methylbutyl]amino]methyl]-1-pyrrolidinecarboxylic acid, phenylmethyl ester To a flame dried, $N_2$ purged 500 ml flask add 6.17 g (S)-2-formyl-1-pyrrolidonecarboxylic acid, phenylmethyl ester, 250 ml dry, distilled THF, 93 g 5 Å molecular sieves (predried at 400° C.) and 5.30 g (S)-glycine, N-(2-amino-4-methylpentyl)-,1,1-dimethyl ethyl ester. Stir at 25° C. overnight. Filter, and strip filtrate in vacuo to a yellow oil, 9.83 g. Add 110 ml dry, absolute ethanol, a few crystals of bromocresol green and 1.38 g sodium cyanoborohydride. Cool to 5° C. and adjust color to green by the dropwise addition of a cold solution of anhydrous hydrogen chloride gas in ethanol over four hours. Add 1.38 g sodium cyanoborohydride, and adjust color to green as previously described. Stir for two days at 25° C. Add 45 g citric acid over one hour with foaming. Strip off ethanol in vacuo and dissolve residue in 250 ml ethyl acetate. Wash organic phase twice with 150 ml H$_2$O. Neutralize aqueous phase by addition of solid sodium bicarbonate and extract twice with 150 ml ethyl acetate. Dry the organic phase over anhydrous magnesium sulfate, filter, and strip in vacuo to a clear oil, 4.8 g. Chromatograph on 200 g silica gel, eluting with methanol. Recover a yellow oil, 3.62 g 37% yield. R$_f$=0.46 on Merck SG60 TLC plates eluted with 10/90 methanol/chloroform. Mass spectra detected the molecular ion of the anticipated product at 448.2. Additional fragmentation supports the proposed structure. The material was sufficiently pure for use in the next step.

EXAMPLE 82

[S-(R*,R*)]2-[[[1-[[(Carboxymethyl)amino]methyl]-3-methylbutyl]amino]methyl]-1-pyrrolidinecarboxylic acid, phenylmethyl ester, hydrochloride (4:7)

To a 100 ml flask containing 3.44 g (S)-2-[[[1-[[[2-(1,1-dimethylethoxy)-2-oxoethyl]amino]methyl]-3-methylbutyl]amino]methyl]-1-pyrrolidinecarboxylic acid, phenyl methyl ester add 50 ml trifluoroacetic acetic acid and stir at 25° C. for 1.5 hours. Strip under vacuum to an oil. Add 50 methylene chloride and strip to an oil. Repeat once. Add 50 ml methylene chloride, saturate with anhydrous hydrogen chloride gas and strip to an oil. Repeat once. Add 50 ml methylene chloride and precipitate by addition of 400 ml anhydrous ethyl ether. Filter the solid and wash with ethyl ether. Dry in vacuo at 37° C. giving a white solid, 3.35 g [α]$_D^{23}$−7.2° (c 1.05, methanol). Mass spectra detected the molecular ion at 392. R$_f$=0.25 on Merck SG60 TLC plates, eluted with 20/80 methanol/chloroform.

EXAMPLE 83

N-Carbobenzyloxy-1-amino-5-bromohexanoic acid

Lys(Z) (40.0 g, 0.14 mol) is taken up in 120 ml cooled 6M HBr/H$_2$O. NaNO$_2$ (10.6 g, 0.15 mol) is added in aliquots at 0° over a 30 minute period. Then the reaction is stirred another five minutes. During this time more hydrobromic acid is added to help dissolve all the Lys (Z). The reaction is extracted three times with ethyl acetate. The organic phases are combined and washed with H$_2$O and dried with MgSO$_4$. The mixture is filtered and the filtrate is evaporated down to an orange oil. This is chromatographed with MeOH/CHCl$_3$ to give 23.2 g of product.

For C$_{14}$H$_{18}$NO$_4$Br.0.1 mol HBr Calc: C, 47.72; H, 5.18; N, 3.98. Found: C, 48.08; H, 5.01; N, 3.98

EXAMPLE 84

Methyl, N-carbobenzyloxy-1-amino-5-bromohexanoate

N-carbobenzyloxy-1-amino-5-bromohexanoic acid (10.1 g, 0.029 mol) is dissolved in methanol and the solution cooled. Gaseous HCl is bubbled into the solution for five minutes. The reaction is stirred without the bath for three hours. The solution is retreated with HCl and stirred 3.5 hours. The reaction is placed in the refrigerator for three days and then evaporated down to 9.0 g of a yellow oil Calc.: C, 50.29; H, 5.63; N, 3.91. Found: C, 49.85; H, 5.17; N, 3.81.

EXAMPLE 85

1-Carbobenzyloxy-2-acetylmercaptomethylpyrrolidine

Triphenylphosphine (33.6 g, 0.128 mol) is dissolved in 150 ml THF and cooled to 0°. 25.2 ml (0.128 mol) of diisopropyl azodicarboxylate (DIAD) is added slowly and the reaction then stirred at 0° for one-half hour. 15.0 g (0.064 mol) of 1-carbobenzyloxy prolinol and 9.2 ml (0.128 mol) of acetylthiol in 75 ml of THF are added dropwise. The reaction is stirred for one hour at 0° and overnight at room temperature. The reaction is evaporated down and the residue chromatographed with CH$_2$Cl$_2$/Hexane 1/1.

For C$_{15}$H$_{19}$NO$_3$S.1/6 mol DIAD Calc.: C, 60.02; H, 6.48; N, 5.70. Found: C, 59.83; H, 6.53; N, 5.41.

EXAMPLE 86

1-Carbobenzyloxy-2-pyrrolidinemethanethiol

This reaction is run under N$_2$.1-Carbobenzyloxy-2-acetylmercaptomethylpyrrolidine (1.7 g, 0.0058 mol) is dissolved in 25 ml CH$_3$CN. To this is added 5.3 g of 54% NH$_2$NH$_2$. The reaction is heated to 50°. After one-half hour the TLC shows complete reaction. It is stirred one more hour and then evaporated down. To the residue is added ether and the solution is washed with dilute HCl solution and then H$_2$O. The organic phase is dried with MgSO$_4$, filtered, and evaporated to 1.4 g of a purple oil. This is chromatographed on silica gel with isopropyl ether to give 1.1 g of an oil.

For C$_{13}$H$_{17}$NO$_2$S.⅛ mol DIAD: Calc.: C, 60.84; H, 6.75; N, 6.33. Found: C, 60.66; H, 6.92; N, 6.30.

EXAMPLE 87

2-[[[1-Carboxy-5-[[[(phenylmethoxy)carbonyl]amino]-pentyl]thio]methyl]-1-pyrrolidine]carboxylic acid, monosodium salt 1-Carbobenzyloxy-2-pyrrolidinemethanethiol 2.7 g, 0.0106 mol) is taken up in THF and cooled to 0°-5°. To this is added 1.7 g (0.043 mol) NaH. Methyl, N-carbobenzyloxy-1-amino-5-bromohexanoate (3.8 g, 0.0106 mol) in THF is then added dropwise. The reaction is stirred overnight allowing the bath to come to room temperature. The THF is evaporated off and the residue is taken up in CH$_2$Cl$_2$ and dilute HCl solution. The organic phase is isolated and washed with Na$_2$CO$_3$ solution. The CH$_2$Cl$_2$ phase is dried with MgSO$_4$. The mixture is filtered and the filtrate evaporated down. The residue is chromatographed with MeOH/CHCl$_3$ to give the product.

Calc.: C, 63.01; H, 6.66; N, 5.44. Found: C, 62.71; H, 6.58; N, 5.40.

EXAMPLE 88

Nε-Carbobenzyloxylysinol, trifluoroacetate salt 5 g (0.0136 m) of BOC-lysinol (Z) is stirred for 15 minutes in 50% TFA/CH$_2$Cl$_2$ at room temperature. The solution is evaporated down. Pet ether and ether are added and then evaporated off. This step is repeated. A solution of pet ether/ether/CH$_2$Cl$_2$ is added and the mixutre cooled. This is then evaporated down to a part oil, part solid which is dissolved in CH$_2$Cl$_2$ and ether is added. A white solid is filtered which is dried under vacuum to give 2.9 g of product, mp 91°-95°.

Calc.: C, 50.52; H, 6.09; N, 7.37. Found: C, 50.50; H, 6.06; N, 7.31.

Another crop of 1.4 g is obtained, mp 90°-95°.

EXAMPLE 89

[S-(R*,R*)]-2-[[[1-(Hydroxymethyl)-5-[[(phenylmethoxy)carbonyl]amino]pentyl]amino]carbonyl]-1-pyrrolidinecarboxylic acid, phenyl methyl ester 1.8 g (0.0074 mol) of Z-Pro is dissolved in $CH_2Cl_2$ and cooled to 5°–10°. To this is added 1.13 g (0.0074 mol) 1-hydroxybenzotriazole, a cold solution of $N\epsilon$-Z-lysinol.TFA (2.8 g, 0.0074 mol) and $Et_3N$ (1.0 ml, 0.0074 mol) in $CH_2Cl_2$, and by 1.7 g (0.0081 mol) of DCC. The reaction is stirred in an ice bath, which is allowed to come to room temperature and then stirred overnight. Acetic acid is added to destroy any unreacted DCC. The reaction is filtered and filtrate is washed with $H_2O$, HCl solution and finally $Na_2CO_3$ solution. The organic phase is dried with $MgSO_4$ and filtered. The filtrate is evaporated down to a residue which is taken up in $CH_2Cl_2$ and filtered. This filtrate is evaporated down and ether added. A solid forms which is recrystallized from ethyl acetate-pet ether to give 2.5 g of product in a 67.9% yield.

Calc.: C, 65.17; H, 7.09; N, 8.44. Found: C, 65.34; H, 7.31; N, 8.25.

$[\alpha]_D^{23} - 28.4°$ (c 0.88 methanol).

EXAMPLE 90

BOC-D-Lys(Z)-GlyNH₂

$GlyNH_2 \cdot HCl$ (2.65 g, 0.024 mol) is dispersed in DMF and to this is added $Et_3N$ (3.35 ml, 0.024 mol) and HOBT (3.7 g, 0.024 mol). 9.0 g (0.024 mol) of BOC-D-Lys(Z) in a large volume of DMF is added and the $GlyNH_2$ goes into solution. The total volume of DMF is 400 ml. The reaction is stirred overnight and then filtered. The solvent is evaporated off and the residue dissolved in $CH_2Cl_2$. This is washed with citric acid solution, $Na_2CO_3$ solution and then NaCl solution, and dried with $MgSO_4$. The mixture is filtered, the filtrate evaporated down and the residue is taken up in ethyl acetate and cooled. The solid is filtered and washed with pet ether. More solid is obtained from the filtrate. Both crops are combined and triturated with ether. 7.5 g of a tan, solid is obtained in a 71% yield:

Calc: C, 57.78; H, 7.39; N, 12.84. Found: C, 58.45; H, 7.27; N, 12.66.

EXAMPLE 91

D-Lys(Z)-GlyNH₂.trifluoroacetate salt

BOC-D-Lys(Z)-GlyNH₂ (7.3 g, 0.017 mol) is dissolved in $CH_2Cl_2$ and an equal volume of trifluoroacetic acid is added. The solution is stirred at room temperature for 15–20 minutes. The reaction is evaporated down and $CH_2Cl_2$ added. This is evaporated down and pet ether, ether and $CH_2Cl_2$ are added. The flask is placed in the refrigerator overnight. The solvent is decanted and a solid is obtained by triturating in ether/pet ether. The product is dried under vacuum to give 6.8 g of a tan solid.

For $C_{16}H_{24}N_4O_4 \cdot 1.2$ mol TFA: Calc: C, 46.70; H, 5.36; N, 11.84. Found: C, 46.58; H, 5.34; N, 11.63.

EXAMPLE 92

[S-(R*,S*)]2-[[[1-[[(2-Amino-2-oxoethy)amino]-5-[[(phenylmethoxy)carbonyl]amino]pentyl]amino]methyl]-1-pyrrolidinecarboxylic acid 1,1-dimethyl ethyl ester D-Lys-GlyNH₂.1.2 TFA (6.65 g, 0.014 mol) is dissolved in methanol and the pH is brought to 7 with $Et_3N$. To this is added BOC-prolinal (2.8 g, 0.014 mol), 3Å molecular sieves (activated) and $NaCNBH_3$ (3.1 g, 0.05 mol). The pH is adjusted to 5 and the reaction is stirred at room temperature over the weekend. The mixture is filtered and the filtrate evaporated down. The residue is taken up in ethyl acetate and washed with citric acid solution, $Na_2CO_3$ solution and then $H_2O$. The organic phase is dried with $MgSO_4$, filtered and evaporated down to 3.9 g of an orange oil. This is chromatographed using flash chromatography with $CH_2Cl_2$-MeOH as eluent. 700 mg of product is obtained.

For $C_{26}H_{41}N_5O_6 \cdot \frac{1}{4}CH_2Cl_2$: Calc.: C, 58.29; H, 7.73, N, 12.95. Found: C, 58.52; H, 7.24; N, 13.07.

EXAMPLE 93

(S)-N-[N⁶-[(Phenylmethoxy)carbonyl]-N²-(2 pyrrolidinylmethyl)-D-lysyl]-glycinamide, trifluoroacetate (salt).

2-[[[1-[[(2-Amino-2-oxoethyl)amino]carbonyl]-5-[[(phenylmethoxy)carbonyl]amino]pentyl]amino]methyl]-1-pyrrolidinecarboxylic acid, 1,1-dimethylethyl ester (1.0 g, 0.0019 mol) is dissolved in $CH_2Cl_2$ and an equal portion of trifluoroacetic acid is added. The solution is stirred at room temperature for 15 minutes. The reaction is evaporated down and the residue dissolved in $CH_2Cl_2$ and reevaporated. This is repeated a number of times to remove the trifluroacetic acid. Ether/pet ether is added and the mixture is cooled. A hygroscopic solid is filtered, dissolved in a solvent and evaporated to a foam. Pet ether is added and a solid is filtered, which is dried under vacuum.

Calc.: C, 46.37; H, 5.45; N, 10.81; F, 17.60. Found: C, 45.04; H, 5.39; N, 11.06; F, 17.83.

$[\alpha]_D^{23} = 7.9°$ (c 1.08, methanol).

EXAMPLE 94

[S-(E)]1,1-Dimethyl ethyl[1-2-methylpropyl)-5-(trimethylsilyl)-2-penten-4-ynyl]carbamate Under nitrogen, a suspension of 84.0 g of 1-trimethylsilyl-propyne-3-triphenylphosphonium bromide (J. Chem. Soc. 1981 (1974) in 1 l tetrahydrofuran is cooled to −80° and treated dropwise with 88.3 ml of a 2.1M solution of n-butyl lithium in hexane. After stirring for 45 minutes at −80°, the mixture is treated dropwise with a solution of 39.9 g of N-(t-butoxycarbonyl)-L-leucinal (Synthesis 676 (1983) in 600 ml of tetrahydrofuran. After stirring at −80° for 30 minutes, the mixture is allowed to warm to room temperature over two hours. The mixture is concentrated to one-half volume under reduced pressure and poured into 1 l of water. The mixture is extracted with ether, then two times with petroleum ether. The combined organic extracts are washed with saturated sodium chloride solution, dried over magnesium sulfate and the solvent removed under reduced pressure. The residue is dissolved in petroleum ether and the insoluble triphenylphosphine is filtered off. Removal of the solvent under reduced pressure gives the crude product. After chromatography on silica gel, eluting with chloroform, there is obtained 34.2 g of [S-(E)]1,1-dimethylethyl[1-2-methylpropyl)-5-(trimethylsilyl)-2-penten-4-ynyl]carbamate sufficiently pure to use in the following reaction.

EXAMPLE 95

[S-(E)]-5-[[(1,1-Dimethylethoxy)carbonyl]amino]-7-methyl-3-octenoic acid

Under nitrogen, a solution of 316 ml of borane (1N in tetrahydrofuran) is cooled in ice and treated dropwise with a solution of 64 ml of cyclohexene in 890 ml of tetrahydrofuran. After stirring at 0° for thirty-five minutes, the solution is treated dropwise with a solution of 27.94 g of [S-(E)]1,1-dimethylethyl[1-(2-methylpropyl)-5-(trimethylsilyl)-2-penten-4-ynyl]carbamate in 110 ml of tetrahydrofuran. After stirring for one-half hour, the solution is treated dropwise with 112 ml of methanol, 157 ml of 2N sodium hydroxide, and then over one-half hour with 102 ml of 30% hydrogen peroxide, keeping the temperature below −10°. The solution is then stirred for one-half hour, and poured into 2.2 l of water containing 112 ml of 2N sodium hydroxide. After extracting three times with ether, the pH is adjusted to 2.0 and the solution extracted three times with ether. The combined ether extracts are washed with saturated sodium chloride solution and dried over magnesium sulfate. Removal of the solvent under reduced pressure and chromatography on silica gel, eluting with chloroform/methanol (95/5) gives 10.7 g [S-(E)]-5-[[(1,1-dimethylethoxy)carbonyl]amino]-7-methyl-3-octenoic acid as an oil suitable for use in subsequent reactions. The product is characterized by converting a small amount to the dicyclohexylamine salt, mp 126°–128∞, $[\alpha]_D^{23} -18°$ (c 1.02, methanol).

EXAMPLE 96

[S-(E)]1,1-Dimethylethyl[5-amino-1-(2-methylpropyl)-2-pentenyl]carbamate

A solution of 6.0 g [S-(E)]-S-[[(1,1-dimethylethoxy)carbonyl]amino]-7-methyl-3-octenoic acid in 60 ml tetrahydrofuran is cooled in ice and treated with 2.44 ml of N-methylmorpholine followed by the dropwise addition of 2.9 ml of isobutylchloroformate. After 5 minutes at 0°, 6.0 ml of concentrated ammonium hydroxide is added and the solution allowed to stir at 0° for one hour. The solvent is removed under reduced pressue and the residue taken up in ethyl acetate, washed with water, 1N citric acid, saturated sodium bicarbonate, and then with saturated sodium chloride. After drying over magnesium sulfate and removal of the solvent under reduced pressue, the residue is chromatographed on silica gel, eluting with chloroform/methanol (9:1). There is obtained 3.5 g of [S-(E)]1,1-dimethylethyl[5-amino-1-(2-methylpropyl)-2-pentenyl]carbamate as an oil which solidifies on standing. The material is suitable for use in the following reaction. A small sample, recrystallized from toluene/hexane has mp 85°–89°.

$[\alpha]_D^{23} +20.9°$ (c, 1.1, methanol).

EXAMPLE 97

[S-(E)]-5-Amino-7-methyl-3-octenamide, monohydrochloride

A solution of 6.23 g of [S-(E)]1,1-dimethylethyl[5-amino-1-(2-methylpropyl)-2-pentenyl]carbamate in 60 ml of trifluoroacetic acid is stirred at room temperature for one hour. The trifluoroacetic acid is removed under reduced pressure, the residue taken up in dichloromethane, and the solvent removed again. The residue is taken up in dichloromethane and hydrogen chloride gas bubbled into the solution for a few minutes. The solvent is then removed under reduced pressure. The residue is taken up in a small amount of dichloromethane and added dropwise to excess ether. The solid is collected and washed with ether. There is obtained 4.14 g of [S-(E)]-5-amino-7-methyl-3-octenamide, monohydrochloride suitable for use in the following reaction, $[\alpha]_D^{23} -20.0°$ (c 1.04, methanol).

EXAMPLE 98

[S-(R*,R*-(E)]-Phenylmethyl 2-[[[5-amino-1-(2-methylpropyl)-5-oxo-2-pentenyl]amino]carbonyl]-1-pyrrolidinecarboxylate To a suspension of 2.0 g of [S-(E)]-5-amino-7-methyl-3-octenamide, monohydrochloride in 50 ml of tetrahydrofuran is added 2.42 g of Z-proline and 1.31 g of hydroxybenzotriazole hydrate. The mixture is cooled in ice and treated with 1.35 ml of triethylamine followed by a solution of 2.0 g of dicyclohexylcarbodiimide in 10 ml of tetrahydrofuran. The solution is kept at 0° for one hour, then at room temperature overnight. The solution is then filtered and the filtrate concentrated under reduced pressure. The residue is taken-up in ethyl acetate and washed with water, 1N citric acid, saturated sodium bicarbonate, and then with saturated sodium chloride. After drying over magnesium sulfate and removal of the solvent under reduced pressure, the residue is chromatographed on silica gel, eluting with chloroform/methanol (95/5). After combining the appropriate fractions and trituating the residue with ethyl acetate/hexane, there is obtained 1.54 g of [S-(R*,R*-(E)]-phenylmethyl 2-[[[5-amino-1-(2-methylpropyl)-5-oxo-2-pentenyl]amino]carbonyl]-1-pyrrolidinecarboxylate, mp 140°–142°, $[\alpha]_D^{23} -73.0°$ (c 1.03, methanol).

EXAMPLE 99

[S-(R*,R*-(E)]-N-[5-Amino-1-(2-methylpropyl)-5-oxo-2-pentenyl]-5-oxo-2-pyrrolidinecarboxyamide To a suspension of 2.1 g of [S-(E)]-5-amino-7-methyl-3-octenamide, monohydrochloride (prepared in Example 97) in 40 ml of N,N-dimethylformamide is added 1.32 of L-pyroglutamic acid, and 1.38 g of hydroxybenzotriazole hydrate. The mixture is cooled in ice and treated with 1.42 ml of triethylamine followed by a solution of 2.1 g of dicyclohexylcarbodiimide in 10 ml of N,N-dimethylformamide. The solution is kept at 0° for one hour, then at room temperature overnight. After filtering to remove dicyclohexylurea, the solvent is removed under high vacuum. The residue is taken up in chloroform and washed twice with water. On cooling the water extracts, hydroxybenzotriazole precipitates and is removed by filtration. The filtrate in lyophilized. The residue is chromatographed on silica gel, eluting with chloroform/methanol (85/15). Combining the appropriate fractions and recrystallizing the residue from acetonitrile gives 1.03 g of [S-(R*,R*-E)]-N-[5-amino-1-(2-methylpropyl)-5-oxo-2-pentenyl]-5-oxo-2-pyrrolidinecarboxyamide, mp 150°–152°, $[\alpha]_D^{23} -39.1°$ (c 1.19, methanol).

We claim:

1. A modified peptide of the formula:

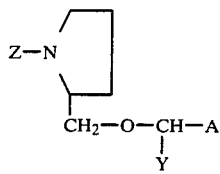

wherein Z is hydrogen, carbobenzyloxy, t-butoxycarbonyl, tosyl, or p-methoxybenzyloxycarbonyl; Y is hydrogen or $CH_2CH(CH_3)_2$; A is selected from the group consisting of —C(O)OH, —C(O)O lower alkyl, —C(O)NH$_2$, —C(O)OCH$_2$C$_6$H$_5$, —C(O)NH(lower alkyl), —C(O)NH(lower alkyl), —C(O)N(lower alkyl)$_2$, —C(O)NHCH$_2$C(O)OH and —C(O)NH(CH$_2$)$_n$S(lower alkyl) in which n is an integer from two to four, or a pharmaceutically acceptable acid addition or base salt thereof.

2. A compound according to claim 1 and being (S)-phenylmethyl 2-[[1-[[(carboxymethyl)amino]carbonyl]-3-methyl-butoxymethyl]-1-pyrrolidinecarboxylate (2-position of pentane chain is RS].

3. A compound according to claim 1 and being (S)-phenylmethyl-2-[[[[(carboxymethyl)amino]carboxy]methoxy]methyl]-1-pyrrolidinecarboxylate.

4. A compound according to claim 1 and being (2S)-phenylmethyl 2-[(1-carboxy-3-methylbutoxy)methyl]-1-pyrrolidinecarboxylate.

5. A compound according to claim 1 and being (S)-phenylmethyl 2-[(carboxymethoxy)methyl]-1-pyrrolidinecarboxylate.

6. A pharmaceutical composition comprising an antidepressant effective amount of a compound according to claim 1 in admixture with a pharmaceutically acceptable carrier or diluent.

7. A method for treating depression in patients suffering therefrom comprising administering to said patient a pharmaceutical composition according to claim 6 in unit dosage form.

* * * * *